United States Patent [19]
Olsen et al.

[11] Patent Number: 5,591,150
[45] Date of Patent: Jan. 7, 1997

[54] SANITARY NAPKIN HAVING A RESILIENT BODY-CONFORMING PORTION

[75] Inventors: Robb E. Olsen, Cincinnati, Ohio; Sandra R. Bittar, Sao Paulo/sp, Brazil; Letha M. Hines, Cincinnati, Ohio; William R. Vinnage, Jr., Cincinnati, Ohio; Melisse N. May, Cincinnati, Ohio; Thomas W. Osborn, III, Cincinnati, Ohio; Nancy B. Doak, Cincinnati, Ohio

[73] Assignee: The Procter and Gamble Company, Cincinnati, Ohio

[21] Appl. No.: 241,430

[22] Filed: May 11, 1994

Related U.S. Application Data

[63] Continuation-in-part of Ser. No. 734,405, Jul. 23, 1991, Pat. No. 5,334,176, Ser. No. 915,133, Jul. 23, 1992, Ser. No. 915,285, Jul. 23, 1992, Pat. No. 5,382,245, Ser. No. 563,879, Nov. 21, 1995, Ser. No. 43,645, Apr. 6, 1993, Pat. No. 5,356,405, Ser. No. 444,079, May 17, 1995, Ser. No. 506,137, Jul. 24, 1995, Ser. No. 520,456, Sep. 19, 1995, Ser. No. 268,869, Jun. 30, 1994, abandoned, Ser. No. 439,931, May 12, 1995, abandoned, Ser. No. 192,240, Feb. 4, 1994, abandoned, and Ser. No. 238,191, May 4, 1994, abandoned, said Ser. No. 563,879, is a continuation of Ser. No. 7,207, Jan. 22, 1993, abandoned, said Ser. No. 444,079, is a continuation of Ser. No. 84,048, Jun. 28, 1993, abandoned, said Ser. No. 506,137, is a continuation of Ser. No. 342,678, Nov. 21, 1994, abandoned, which is a continuation of Ser. No. 96,092, Jul. 23, 1993, abandoned, said Ser. No. 520,456, is a continuation of Ser. No. 161,215, Dec. 2, 1993, abandoned, said Ser. No. 268,869, is a continuation of Ser. No. 165,757, Dec. 13, 1993, abandoned, said Ser. No. 439,931, is a continuation of Ser. No. 166,660, Dec. 13, 1993, abandoned.

[51] Int. Cl.[6] .............................. A61F 13/15; A61F 13/20
[52] U.S. Cl. .................. 604/385.1; 604/387; 604/366; 604/365; 604/380
[58] Field of Search .................... 604/367, 370, 604/385.1, 365, 366, 380, 387

[56] References Cited

U.S. PATENT DOCUMENTS

| | | |
|---|---|---|
| 2,064,431 | 12/1936 | Jurgensen . |
| 2,747,575 | 5/1956 | Mercer . |
| 3,343,543 | 9/1967 | Glassman . |
| 3,430,630 | 3/1969 | Megison et al. . |
| 3,570,493 | 3/1971 | Olsson . |
| 3,575,174 | 4/1971 | Mogor . |
| 3,696,187 | 10/1972 | Glassman . |
| 4,195,634 | 4/1980 | DiSalvo et al. . |
| 4,405,326 | 9/1983 | Lenaghan . |
| 4,631,062 | 12/1986 | Lassen et al. . |
| 4,642,110 | 2/1987 | Dudek ............................ 604/385.1 |
| 4,701,177 | 10/1987 | Ellis et al. . |
| 4,886,513 | 12/1989 | Mason, Jr. et al. .............. 604/385.1 |
| 5,171,302 | 12/1992 | Buell . |
| 5,300,055 | 4/1994 | Buell . |
| 5,324,278 | 6/1994 | Visscher et al. ................ 604/385.1 |
| 5,383,869 | 1/1995 | Osborn, III ..................... 604/385.1 |

FOREIGN PATENT DOCUMENTS

| | | |
|---|---|---|
| 0136524A1 | 4/1985 | European Pat. Off. . |
| 0140470A1 | 5/1985 | European Pat. Off. . |
| 0162451A1 | 11/1985 | European Pat. Off. . |
| 0176853B1 | 4/1986 | European Pat. Off. . |
| 0298348A1 | 1/1989 | European Pat. Off. . |
| 0607985A1 | 7/1994 | European Pat. Off. . |

*Primary Examiner*—John G. Weiss
*Assistant Examiner*—Rob Clarke
*Attorney, Agent, or Firm*—Edward J. Milbrada; Jeffrey V. Bamber; Steven W. Miller

[57] ABSTRACT

An absorbent article, such as a sanitary napkin having a body-conforming portion or component that is capable of continuously adusting is provided. The body-conforming component, in one embodiment, is in the form of a resilient insert which has multiple arcuate portions in use. The insert has a central arcuate portion that provides the sanitary napkin with a convex upward shape in use and a pair of lateral arcuate portions that form barriers to the flow of liquid exudates. The multiple arcuate portions can either be pre-formed into the insert, or the insert can be provided in the form of a relatively flat piece that is provided with areas of different stiffness that form arcuate portions during use.

41 Claims, 8 Drawing Sheets

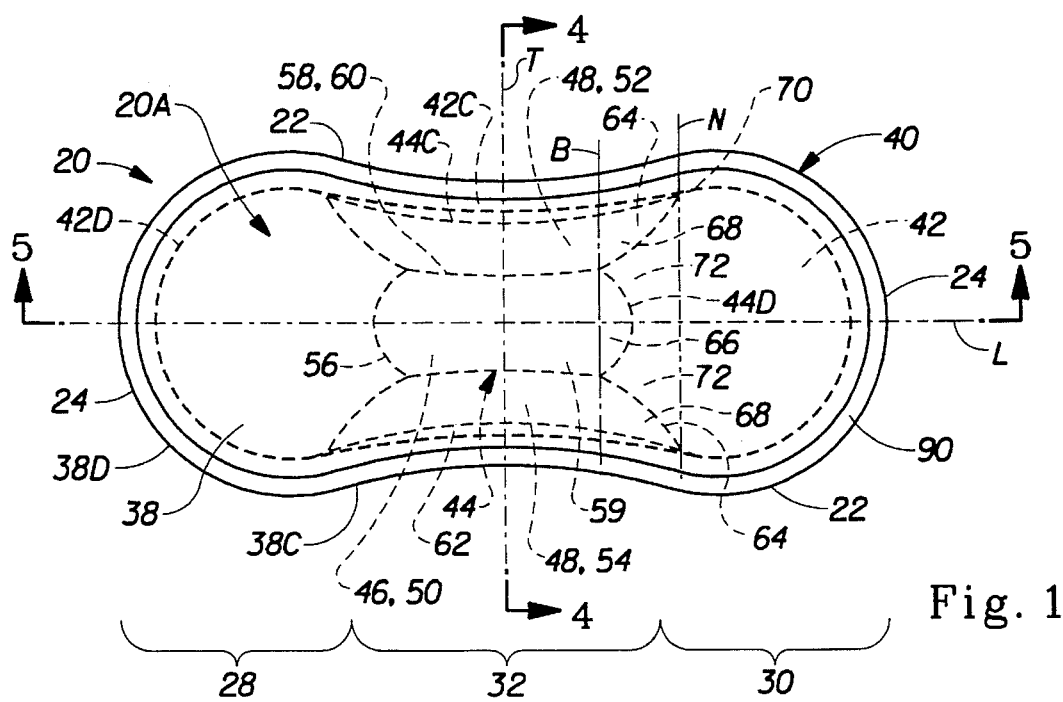
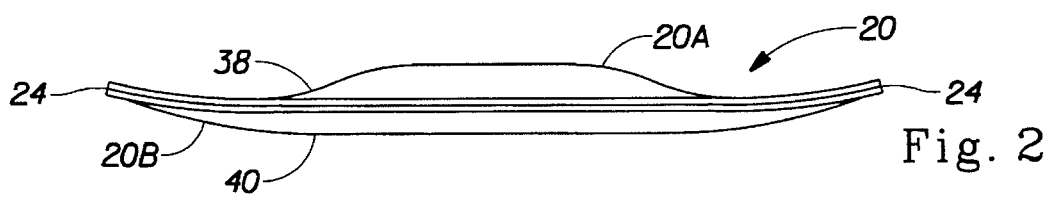
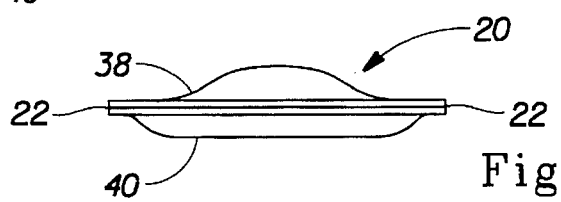
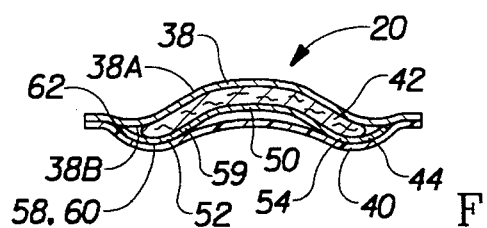
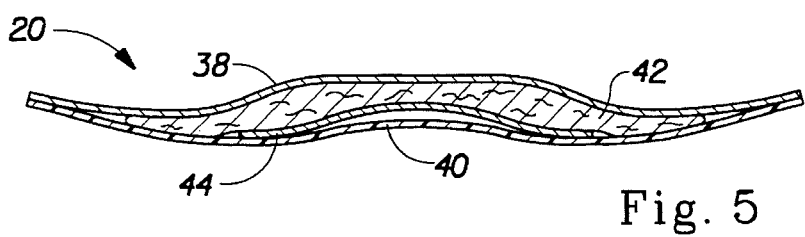

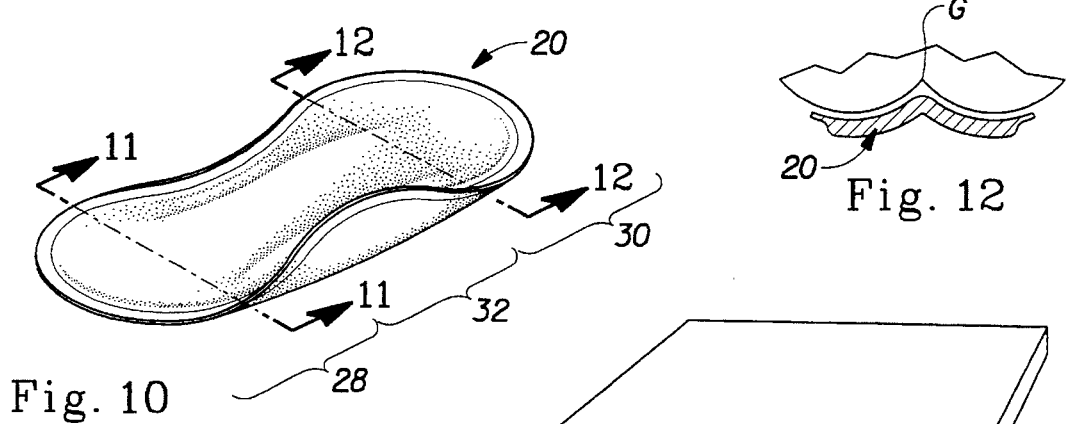
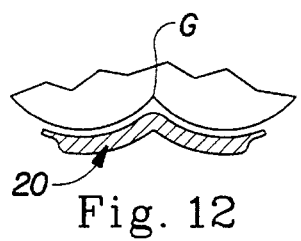
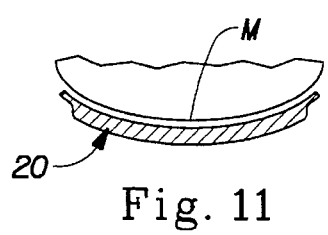
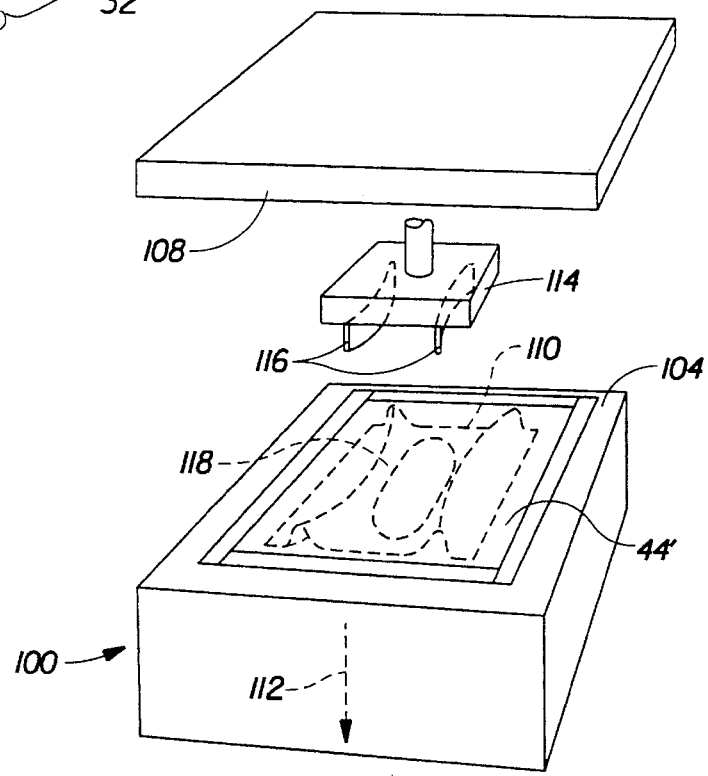
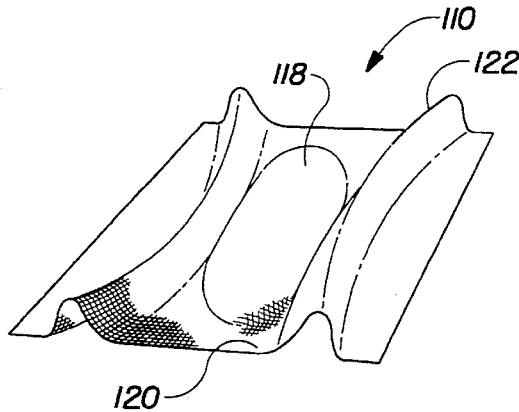

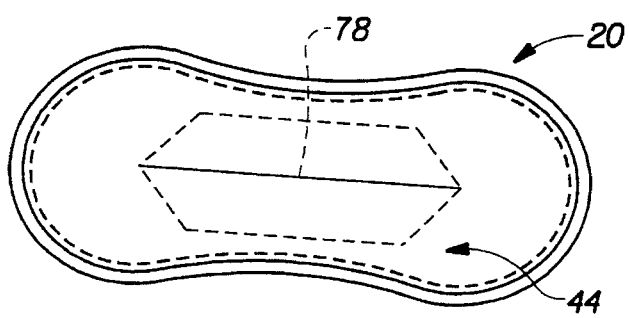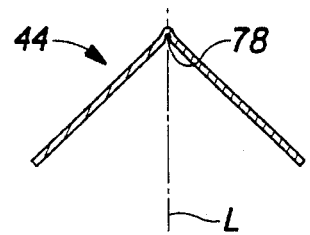
Fig. 15A Fig. 15B
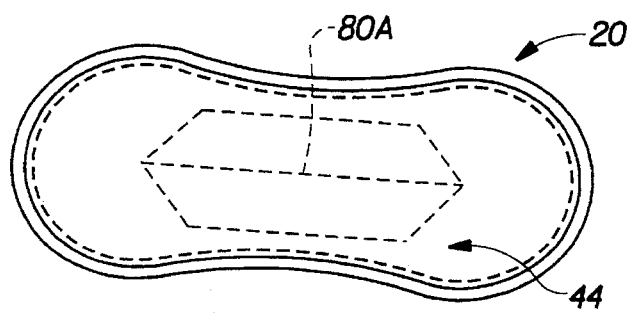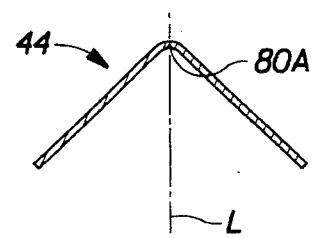
Fig. 16A Fig. 16B
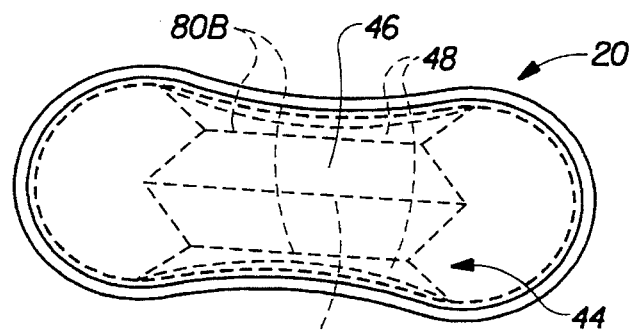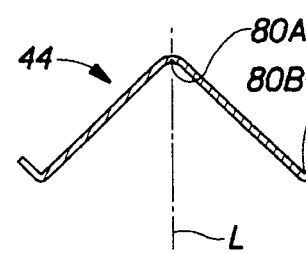
Fig. 17A Fig. 17B
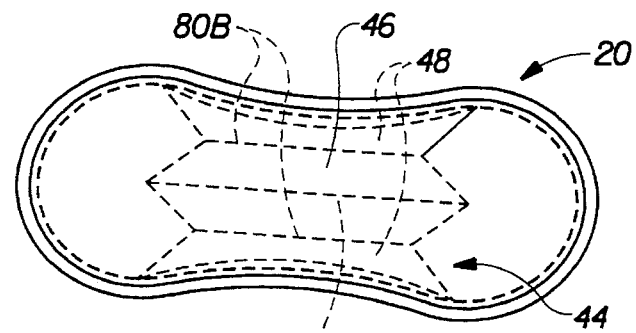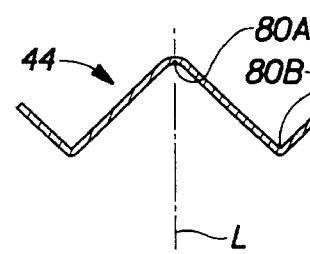
Fig. 18A Fig. 18B

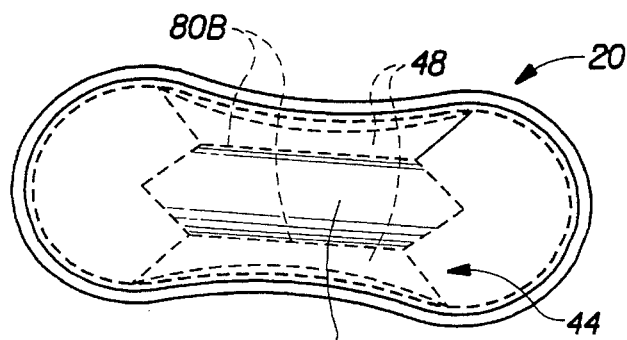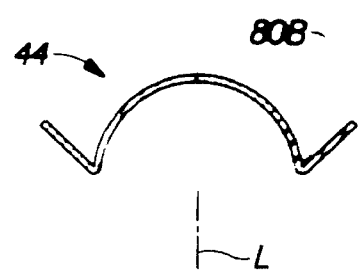
Fig. 19A    Fig. 19B
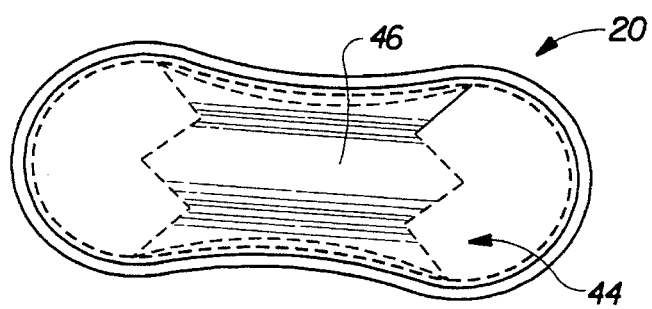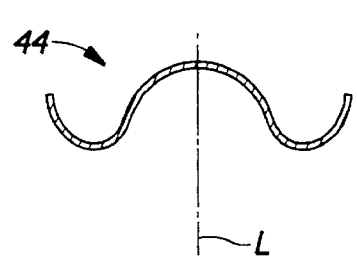
Fig. 20A    Fig. 20B
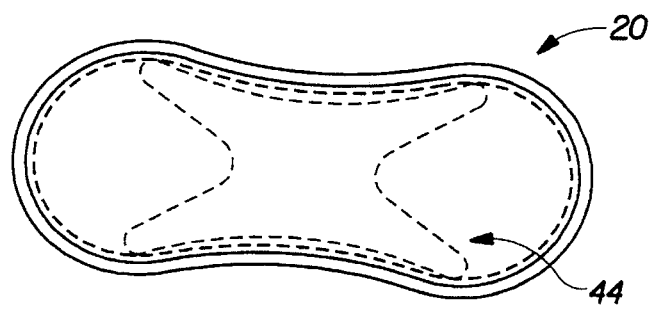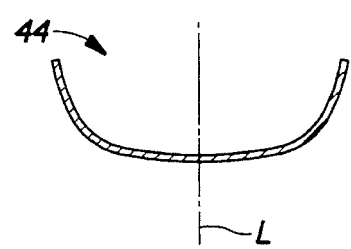
Fig. 21A    Fig. 21B
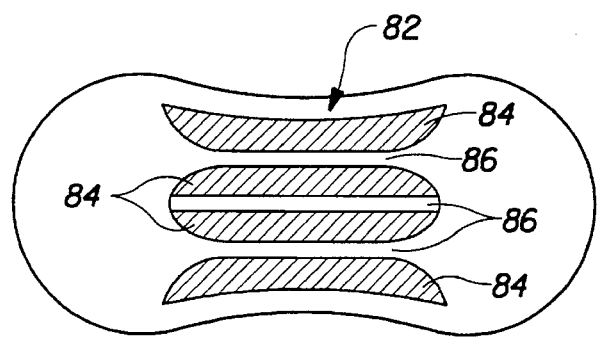
Fig. 22

5,591,150

SANITARY NAPKIN HAVING A RESILIENT BODY-CONFORMING PORTION

This is a continuation-in-part of the following U.S. patent applications: Ser. No. 07/734,405, filed Jul. 23, 1991, U.S. Pat. No. 5,334,176; Ser. No. 07/915,133, filed Jul. 23, 1992, pending; Ser. No. 07/915,285, filed Jul. 23, 1992, U.S. Pat. No. 5,382,245; Ser. No. 08/563,879, filed Nov. 21, 1995, allowed, which is a continuation of Ser. No. 08/007,207, filed Jan. 22, 1993, now abandoned; Ser. No. 08/043,645, filed Apr. 6, 1993, U.S. Pat. No. 5,356,405; Ser. No. 08/444,079, filed May 17, 1995, pending, which is a continuation of Ser. No. 08/084,048, filed Jun. 28, 1993, abandoned; Ser. No. 08/506,137, filed Jul. 24, 1995, pending, which is a continuation of Ser. No. 08/342,678, filed Nov. 21, 1994, abandoned, which is a continuation of Ser. No. 08/096,092, filed Jul. 23, 1993, abandoned; Ser. No. 08/520,456, filed Sep. 19, 1995, pending, which is a continuation of Ser. No. 08/161,215, filed Dec. 2, 1993, abandoned; Ser. No. 08/268,869, filed Jun. 30, 1994, abandoned, which is a continuation of Ser. No. 08/165,757, filed Dec. 13, 1993, abandoned; Ser. No. 08/439,931, filed May 12, 1995, abandoned, which is a continuation of Ser. No. 08/166,660, filed Dec. 13, 1993, abandoned; Ser. No. 08/192,240, filed Feb. 4, 1994, abandoned; and Ser. No. 08/238,191, filed May 4, 1994, abandoned.

FIELD OF THE INVENTION

The present invention relates to absorbent articles such as sanitary napkins, pantiliners, and incontinence pads. More particularly, the present invention relates to sanitary napkins that have resilient body-conforming portions or components that are capable of continuously adjusting to provide enhanced fit and comfort.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineal area of the body.

It has been found that it is desirable to maintain absorbent articles in close contact with the wearer's body. The maintenance of close contact of such products to the perineal area is referred to herein as body contact. The importance of body contact is known in the art for its role in allowing the absorbent article to absorb the body exudates at their source. Achieving good body contact limits the chance for the body exudates to flow off of or out of the absorbent article.

The sanitary napkin art contains examples of sanitary napkins having mechanisms to resist distortion of the napkin in use as well as to attempt to maintain contact with the wearer's body. For example, various types of absorbent products with resilient members are known and disclosed in the patent literature. They generally fall into one of three classes. The first class of absorbent articles with inserts are those which contain flat inserts that are primarily intended to resist distortion of the absorbent product such as the articles disclosed in UK Patent Application 2,168,612 entitled "Sanitary Towel with Resilient Insert" published in the name of Fennimore on Jun. 25, 1986 and in U.S. Pat. No. 4,195,634 entitled "Sanitary Napkin with Resilient Stiffening Means" issued to DiSalvo et al. on Apr. 1, 1980.

The second class of absorbent articles contain pre-shaped resilient structures or inserts such as those disclosed in U.S. Pat. No. 4,886,513 entitled "Absorbent Pad with Reinforcing Member to Resist Deformation" issued to Mason, Jr., et al. on Dec. 12, 1989. Another example is disclosed in PCT International Publication No. WO 91/03999 (assigned to Molnycke), published in the name of Lindquist on Apr. 4, 1991. These inserts generally do not allow for comfortable and continuous contact with the body in that they are typically limited to a shape that does not closely resemble the shape of a woman's anatomy.

These approaches suffer from the drawback that they do not generally provide for continuous adjustment to the shape of the wearer's anatomy and contact with the wearer's body. Previous designs intended to promote body contact are also not believed to be suitable when applied across the broad range of women's body sizes and dimensions.

The third class are sanitary napkins and other absorbent products which offer enhanced fit and comfort through a construction that promotes a continuous self-conforming anatomical cooperation of the sanitary napkin to the body. Absorbent articles in this class are disclosed in U.S. Pat. Nos. 5,171,302 and 5,197,959 issued to Buell on Dec. 15, 1992 and Mar. 30, 1993, respectively. This continuous self-conforming anatomical cooperation is achieved by a flexure resistant deformation element that causes the body facing surface of the sanitary napkin to stay in contact with the body. The lateral compressive forces of the wearer's thighs are used to cause a convex upward shaping of the sanitary napkin. In a preferred embodiment, the deformation element has a "W" shaped cross section with the center of the sanitary napkin being curved convexly upward relative to the wearer's body.

While the technology described in the Buell patents provides comfortable body contact, the search for improved and alternative absorbent articles has continued. In particular, it is desirable to provide good body contact such as that described above in an even more comfortable manner in sanitary napkins having a variety of shapes, sizes, and thickness, but especially in ultra thin absorbent articles (that is, those with calipers of less than about 3 mm).

Thus, a need exists for an absorbent article, such as a sanitary napkin, that is provided with an improved mechanism for maintaining the sanitary napkin in contact with the wearer's body while offering increased comfort.

It is, therefore, an object of the present invention to provide an absorbent article, such as a sanitary napkin, that is provided with an improved mechanism for maintaining the sanitary napkin in contact with the wearer's body. This improved mechanism is intended to increase the opportunity for body contact by elevating the center area of the absorbent article with a resilient component that allows the absorbent article to maintain maximum body contact through the various ranges of motion of the wearer while still providing maximum comfort to the wearer, especially in an ultra thin absorbent article.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin comprises a liquid pervious topsheet, a liquid impervious backsheet joined to the topsheet, and an absorbent core positioned between the topsheet and the backsheet. The sanitary napkin is provided with a resilient body-conforming portion or component that preferably has multiple arcuate portions in use.

In one preferred embodiment, the body-conforming component of the sanitary napkin is a resilient insert. The insert is shaped to provide a maximum area of contact with the wearer's body in the center, lateral side barriers, and improved comfort by minimizing the resiliency of the insert in particular areas of the sanitary napkin. The multiple arcuate portions can either be pre-formed into the insert, or the insert can be a relatively flat insert which is provided with areas of different stiffness that form into arcuate portions during use. The resilient insert is preferably positioned in the central region of the sanitary napkin so that if the insert is used in a thin, flexible sanitary napkin, the end regions of the sanitary napkin remain highly flexible. The resilient insert can be positioned above the absorbent core, below the absorbent core, or it can comprise a portion of the absorbent core. If the insert comprises part of the absorbent core or is positioned above the absorbent core, it is preferably liquid pervious and absorbent. If the insert is positioned under the absorbent core, it may be impervious.

In a particularly preferred embodiment, the insert (or other body-conformity feature) has a "butterfly" plan view shape which comprises a central body, a pair of lateral side portions, a pair of longitudinal side edges, and a pair of end edges. The shape of the insert differs from those of prior art inserts in that at least one of said end edges has points of maximum displacement and gaps between the central body and the lateral side portions. This configuration assists the ends of the sanitary napkin in conforming to the shape of the wearer's body and ensures a smooth transition between the central region to the end regions of the sanitary napkin. The insert is also provided with a novel combination of arcuate portions and/or stiffness and compression lines which force the sanitary napkin to elevate in the center so contact with the introitus (vaginal opening) is maximized, allowing the sanitary napkin to conform to the body in an arc shape without bunching. The insert has arcuate side barriers so the edges of both the insert and sanitary napkin resiliently bend laterally to form side barriers in use. These arcuate shapes are designed to specific parameters to allow accurate deformation around the dimensions set by anatomy to accommodate the clitoral and anal regions. This allows for improved body contact with improved comfort to the wearer. Further improvements over the previous technology include forming an insert out of thermally bondable synthetic materials that are thin in caliper so that the insert can be used with ultra thin products.

Alternatively preferred embodiments of the present invention may be achieved through variations in the levels of stiffness and resiliency (i.e., selective stiffeners) that can be obtained by heating or otherwise treating regions of the sanitary napkin, employing different materials (single or multiple layers), and/or by core/insert integration, and fastener (attachment) patterns.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 1 is a top plan view of a preferred embodiment of the sanitary napkin of the present invention.

FIG. 2 is a side elevational view of the sanitary napkin shown in FIG. 1.

FIG. 3 is an end view of the sanitary napkin shown in FIG. 1.

FIG. 4 is a sectional view taken along line 4—4 of the sanitary napkin shown in FIG. 1 before use.

FIG. 5 is a sectional view taken along line 5—5 of the sanitary napkin shown in FIG. 1 before use.

FIG. 10 is a full length view of the sanitary napkin shown in FIG. 1 in an in-use configuration showing the conforming center and flexible ends.

FIG. 11 is a schematic cross-sectional view showing the shape that the sanitary napkin of the present invention takes adjacent to the wearer's mons region.

FIG. 12 is a schematic cross-section view showing the shape that the sanitary napkin assumes adjacent the crevice between the wearer's buttocks ("gluteal groove").

FIG. 13 is a schematic perspective view of a vacuum-forming apparatus used to make a curved insert.

FIG. 14 is a perspective view of the wire screen used for vacuum forming the insert.

FIG. 15A is a perspective view of a sanitary napkin with a first alternative insert configuration.

FIG. 15B is a cross-sectional view of the shape the first alternative insert configuration takes in use.

FIG. 16A is a perspective view of a sanitary napkin with a second alternative insert configuration.

FIG. 16B is a cross-sectional view of the shape the second alternative insert configuration takes in use.

FIG. 17A is a perspective view of a sanitary napkin with a third alternative insert configuration.

FIG. 17B is a cross-sectional view of the shape the third alternative insert configuration takes in use.

FIG. 18A is a perspective view of a sanitary napkin with a fourth alternative insert configuration.

FIG. 18B is a cross-sectional view of the shape the fourth alternative insert configuration takes in use.

FIG. 19A is a perspective view of a sanitary napkin with a fifth alternative insert configuration.

FIG. 19B is a cross-sectional view of the shape the fifth alternative insert configuration takes in use.

FIG. 20A is a perspective view of a sanitary napkin with a sixth alternative insert configuration.

FIG. 20B is a cross-sectional view of the shape the sixth alternative insert configuration takes in use.

FIG. 21A is a perspective view of a sanitary napkin with a seventh alternative insert configuration.

FIG. 21B is a cross-sectional view of the shape the seventh alternative insert configuration takes in use.

FIG. 22 is a plan view of a component of an alternative sanitary napkin which is provided with a selective stiffener.

DETAILED DESCRIPTION OF THE INVENTION

Figure 6:
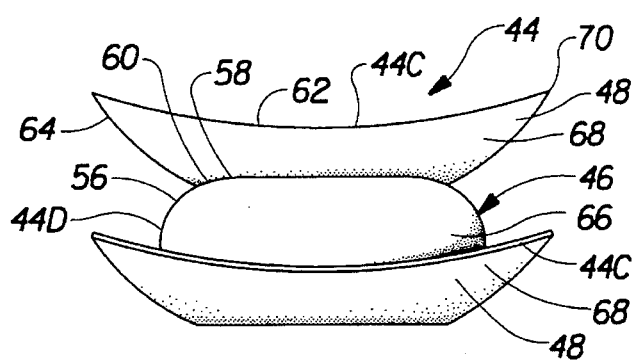
FIG. 6 is a perspective view of a preferred arcuate insert embodiment.

1. General Characteristics of the Absorbent Article

The overall characteristics of the absorbent article of the present invention will be discussed first. FIGS. 1–5 show a preferred embodiment of a disposable absorbent article of the present invention 20. The present invention relates to absorbent articles that have resilient body-conforming portions or components that are capable of continuously adjusting to provide enhanced fit and comfort.

The term "absorbent article," as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinence pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as panty liners, or other absorbent articles such as incontinence pads, and the like.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the sanitary napkin 20 has two spaced apart longitudinal edges 22, two spaced apart transverse or end edges (or "ends") 24, and four corners 27, which together form the periphery 26 of the sanitary napkin 20. The sanitary napkin 20 also has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the sanitary napkin 20. A detailed description of the central region 32 and the two end regions 28 and 30 is contained in U.S. Pat. No. 4,690,680 issued to Higgins on Sep. 1, 1987.

The sanitary napkin 20 can be of any thickness, including relatively thick, relatively thin, or even very thin. The embodiment of the sanitary napkin 20 shown in FIGS. 1–5 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 as described in U.S. Pat. Nos. 4,950,264 and 5,009,653 issued to Osborn preferably has a caliper of less than about 3 millimeters. The thin sanitary napkin 20 shown should also be preferably relatively flexible, so that it is comfortable for the wearer.

FIG. 4 shows the individual components of one embodiment of the sanitary napkin 20 of the present invention. The sanitary napkin shown in FIG. 4 generally comprises four primary components. These include a liquid pervious topsheet 38, a liquid impervious backsheet (or "barrier means") 40, an absorbent core 42 positioned between the topsheet 38 and the backsheet 40, and a resilient insert, such as arcuate shaped insert 44. In other embodiments, the function of the insert can be served by modifying one of the other components of the sanitary napkin, and the insert omitted from the sanitary napkin structure.

2. The Individual Components of the Sanitary Napkin and the Assembly of the Same.

The individual components which may be suitable for the various embodiments of the sanitary napkin 20 of the present invention will now be looked at in greater detail with reference to FIGS. 1–5.

A. The Topsheet

The topsheet 38 comprises a first liquid pervious component. When the sanitary napkin 20 is in use, the topsheet 38 is in close proximity to the skin of the user. The topsheet 38 is preferably as compliant, soft feeling, and non-irritating to the user's skin as possible. The topsheet 38 should further exhibit good strikethrough and a reduced tendency to rewet, permitting bodily discharges to rapidly penetrate it and flow toward the core 42, but not allowing such discharges to flow back through the topsheet 38 to the wearer's skin.

The topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has two longitudinal edges 38C and two end edges 38D.

(A similar numbering system applies to the other components of the sanitary napkin. That is, the side of the component facing the wearer's body can be designated by the number of the component and a reference letter "A". The side facing the wearer's undergarments can be designated by the number of the component and the letter "B". The side and end edges can be designated by the number of the component and the reference letters "C" and "D", respectively.)

A suitable topsheet 38 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can be comprised of natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. When the topsheet 38 comprises a nonwoven web, the web may be spunbonded, carded, wet-laid, meltblown, hydroentangled, combinations of the above, or the like.

Apertured films are generally preferred for the topsheet 38 because they are pervious to liquids and, if properly apertured, have a reduced tendency to allow liquids to pass back through and rewet the wearer's skin. Suitable apertured films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991. A particularly suitable topsheet 38 is made in accordance with U.S. Pat. No. 4,342,314 issued to Radel and U.S. Pat. No. 4,463,045 issued to Ahr, et al. A topsheet 38 made of model X-3265 or model P1552 apertured formed film sold by Tredegar Corporation of Terre Haute, Ind. has been found to work well.

In a preferred embodiment, the topsheet 38 is rendered hydrophilic so that liquids will transfer through the topsheet 38 faster. This will diminish the likelihood that body exudates will flow off the topsheet rather than being drawn through the topsheet and being absorbed by the absorbent core. The topsheet can be rendered hydrophilic by treating it with surfactants. Suitable methods of applying surfactants are described in U.S. Pat. Nos. 4,950,254 and 5,009,653 issued to Osborn.

In addition, in preferred embodiments, the inner surface 38B of topsheet 38 is maintained in contacting relation with an underlying absorbent layer. This contacting relationship results in liquid penetrating topsheet 38 faster. The topsheet 38 can be maintained in contact with an underlying absorbent component by constructing the napkin so that the topsheet is held snuggly against the absorbent component, or by some suitable attachment means, such as by applying adhesives between the topsheet and the underlying component, by entangling the fibers of the underlying layer with the topsheet, by fusing the topsheet 38 to an underlying absorbent layer by a plurality of discrete individual fusion bonds, or by any means known in the art. For example, the topsheet 38 may be secured to the underlying absorbent component by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., under the designation HL-1258 or H-2031. The attachment means preferably comprises an open pattern network of filaments of adhesive as is disclosed in U.S. Pat. No. 4,573,986 issued to Minetola, et al. on Mar. 4, 1986. Exemplary attachment means comprising an open pattern network of filaments comprises several lines of adhesive filaments swirled into a spiral pattern are illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989.

B. The Absorbent Core

The absorbent core 42 is positioned between the topsheet 38 and the backsheet 40. The absorbent core 42 provides the means for absorbing menses and other body fluids.

The absorbent core 42 need not have an absorbent capacity much greater than the total amount of body fluids anticipated to be absorbed. The absorbent core 42 is generally compressible, conformable, and non-irritating to the user's skin. It can comprise any material used in the art for such purpose including natural materials and synthetic materials. Non-limiting examples of such materials include natural materials such as comminuted wood pulp (which is generally referred to as airfelt), creped cellulose wadding, hydrogel-forming polymeric gelling agents, modified cross-linked cellulose fibers (such as those described in U.S. Pat. No. 5,217,445 issued to Young, et al. on Jun. 8, 1993), capillary channel fibers (that is, fibers having intra-fiber capillary channels such as those described in U.S. Pat. No. 5,200,248 issued to Thompson, et al. on Apr. 6, 1993), absorbent foams, absorbent sponges, synthetic staple fibers, polymeric fibers, peat moss, or any equivalent material or combinations of materials.

The polymeric gelling agents listed above may also be referred to as "absorbent gelling materials" or "superabsorbent materials". Polymeric gelling agents are those materials which, upon contact with liquids such as water or other body liquids, imbibe such liquids and thereby form hydrogels. In this manner, liquids discharged into the absorbent core 42 can be acquired and held by the polymeric gelling agent, thereby providing the absorbent articles with enhanced absorbent capacity and/or improved liquid retention performance. The polymeric gelling agent which is employed in the absorbent core 42 will generally comprise particles of a substantially water-insoluble, slightly cross-linked, partially neutralized, hydrogel-forming polymer material. The polymeric gelling agent can be in many forms, including in the form of particles, flakes, or fibers.

In one preferred embodiment, the absorbent core 42 is a laminate. The laminate is comprised of a layer of superabsorbent polymer material, such as in the form of particles, disposed between two air-laid tissues, first and second tissue layers. The first and second tissue layers provide containment of the superabsorbent polymer material, improve lateral wicking of the absorbed exudates throughout the absorbent core 42 and provide a degree of absorbency. The tissue layers can be comprised of a single tissue web which is folded with the superabsorbent material particles between, or two separate sheets of the same (or different) tissue.

A suitable laminate is a superabsorbent laminate known as WATER-LOCK L535 available from the Grain Processing Corporation of Muscatine, Iowa (WATERLOCK registered TM by Grain Processing Corporation). Such superabsorbent laminates are disclosed in U.S. Pat. No. 4,467,012, issued to Pedersen et al. on Aug. 21, 1984, U.S. Pat. No. 4,260,443, issued to Lindsay et al. on Apr. 7, 1981, and U.S. Pat. No. 4,578,068 issued to Kramer, et al. on Mar. 25, 1986.

Particularly preferred absorbent cores for use in the sanitary napkin of the present invention comprise thermally bonded layers formed from a mixture of hydrophilic cellulosic fibers and thermoplastic material wherein the thermoplastic fibers in each layer are thermally bonded and densified. Some preferred thermally bonded absorbent materials are described in greater detail below in conjunction with the description of the resilient insert. Absorbent cores made of such materials are further described in U.S. patent application Ser. No. 08/141,156, entitled "Catamenial Absorbent Structures Having Thermally Bonded Layers for Improved Handling of Menstrual Fluids, and Their Use in Catamenial Pads Having Improved Fit and Comfort" filed in the name of Richards, et al. on Oct. 21, 1993 (P&G Case 5051).

C. The Backsheet

The backsheet 40 prevents the exudates absorbed and contained in the absorbent core 42 from wetting articles which contact the sanitary napkin 20 such as pants, pajamas and undergarments. The backsheet 40 is impervious to liquids (e.g., menses and/or urine). The backsheet 40 is preferably manufactured from a thin plastic film, although other flexible liquid impervious materials may also be used.

The backsheet 40 may comprise a woven or nonwoven material, polymeric films such as thermoplastic films of polyethylene or polypropylene, or composite materials such as a film-coated nonwoven material. A suitable composite backsheet material is nonwoven/film laminate described in U.S. Pat. No. 5,007,906 issued to Osborn Apr. 16, 1991. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., particularly with the pantiliner devices described herein.

D. The Resilient Body-Conforming Component

The resilient body-conforming component is a continuously adjusting element that serves to adapt to the shape of the wearer's body when the wearer moves and to keep the body-facing surface of the sanitary napkin and the underlying absorbent material in close proximity to the wearer's body. The resilient body-conforming component can, as noted above, be provided in a number of forms, including separate inserts, or in other components of the sanitary napkin that are modified to provide the function of the separate inserts. The following description discusses several non-limiting variations of such a component.

(1) Curved Inserts

The sanitary napkin 20 shown in FIGS. 1–5 is provided with a curved resilient insert 44 which is in one preferred configuration. The overall plan view shape of the resilient insert 44 can be thought of as resembling the shape of a butterfly. In plan view (FIG. 1), the insert 44 has a pair of concave inwardly-oriented longitudinal side edges 44C and a pair of curved "W"-shaped end edges 44D. The butterfly-shaped insert 44 comprises a central body 46 and a pair of wings (or lateral side portions) 48. The central body 46 is defined by a longitudinal edge 58 adjacent each of the wings 48 and a pair of ends 56. The wings 48 each have a proximal edge 60 where they emanate from the longitudinal edge 58 of the central body 46, a distal edge 62 spaced away from the central body, and a pair of ends 64. The end edges 44D of the insert 44 comprise both the ends 56 of the central body 46 of the butterfly-shaped insert and the ends 64 of the wings 48.

The configuration of the insert 44, particularly the configuration of the end edges 44D of the insert, is important to the way the insert functions. As shown in FIG. 1, the end edges 44D of the insert can also be thought of as defining a base (shown in the form of an imaginary baseline, B, at the base of the W-shaped ends) and three projections beyond the base line B. These three projections include a central projection (the hump portion of the W) 66 and two wing end projections (or wing end portions) 68. The end edges 44D of the insert are preferably arranged so that the base B of the end edges 44D are the points on the end edges that are located closest to the transverse centerline, T, of the sanitary napkin, and the central projection, or hump portion 66 is located along the longitudinal centerline L. FIG. 1 shows that the ends 64 of the wings 48 of the insert 44 comprise the legs of the W-shape. The legs extend from the base of the W-shape to the tips of the wings (wing tips) 70. These legs or ends 64 of the wings 48 are slightly curved in the embodiment shown in FIG. 1. FIG. 4 shows that in cross-section, the insert 44 comprises three arcuate portions. These include a central arcuate portion 50 and two lateral side arcuate portions 52 and 54. The overall cross-sectional shape of the insert 44 can be thought of as resembling a sine curve. The sine curve shape has one curved portion with a relatively large wavelength and large radius of curvature and two curved portions (one on each side of the large curve) with smaller wavelengths and smaller radii of curvature.

The central arcuate portion 50 comprises at least part of the central body 46 of the insert that was shown in plan view. The central arcuate portion 50 is said to comprise "at least part of" the central body 46 shown in plan view since the curvature of the central arcuate portion 50 and the lateral side arcuate portions 52 and 54 do not necessarily terminate and originate (respectively) precisely at the longitudinal edges 58 of the central body 46. There is preferably a gradual transition between the curvature of the central arcuate portion 50 and the lateral side arcuate portions 52 and 54 which occurs at transition areas 59 that are located between the midpoint, P, of the central arcuate portion 50 and the longitudinal edge 58 of the central body 46. The lateral side arcuate portions 52 and 54, therefore, comprise the wings 48 of the butterfly and a portion of the central body 46 of the insert when it is shown in plan view. The relationship between the arcuate portions of the insert 44 and the portions of the insert identified in the plan view is shown in greater detail in perspective view, FIG. 6.

The central arcuate portion 50 and the lateral arcuate portions 52 and 54 of the insert 44 each serve a different function when the sanitary napkin 20 is worn. The central arcuate portion 50 forms a raised center portion. The central arcuate portion 50 defines an arc that is convex toward the wearer's body in use. The central arcuate portion 50 is curved toward the wearer's introitus adjacent to the perineal area to provide maximum body contact.

The lateral arcuate portions (left side arcuate portion 52 and right side arcuate portion 54) are located on either side of the central arcuate portion 50. The lateral arcuate portions 52 and 54 are concave toward the wearer's body in use. The lateral arcuate portions 52 and 54 form barriers to the flow of bodily exudates in the transverse direction. This is the type of exudate movement that may lead to staining of the wearer's panties may be referred to herein as "side soiling." The lateral arcuate portions 52 and 54 and the central arcuate portion 50 of the insert 44 are configured so that the insert 44 forms a discrete "W" cross-sectional shape in use (see FIG. 8).

The insert 44 is shown in FIG. 1 as being symmetrical about the longitudinal centerline L. The insert 44 is preferably symmetrical about the longitudinal centerline so that it behaves similarly at both longitudinal edges 22 of the sanitary napkin 20 when the sanitary napkin is compressed by the wearer's thighs. The longitudinal edges 44C of the insert 44 are preferably concave as shown in FIG. 1, but is also within the scope of the present invention for the longitudinal edges 44C of the insert to be straight, or to have some other suitable plan view configuration.

The insert 44 is also preferably symmetrical about the transverse centerline T, but it need not be. For instance, the insert 44 may only have one end edge 44D with the preferred W-shape shown in FIG. 1. The other end edge 44D can be a straight line, a curved line, etc. At least one of the end edges 44D of the insert 44, however, preferably has the three projections beyond the imaginary base line B described above.

Figure 6A:
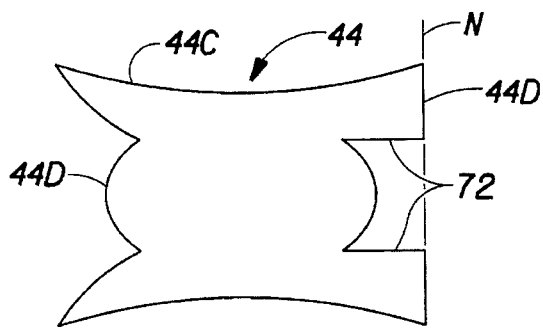
FIG. 6A is a plan view of an alternative insert which has slits along one of its end edges.

An alternative way of describing the configuration of the end edge 44D of the insert 44 is to view the end edge 44D in terms of the gaps or spaces between the three projections. For example, as shown in FIG. 1, instead of using the imaginary base line, B, as the reference line, an imaginary straight line, N, can be drawn between the point or points on the end edge 44D of the insert 44 that are most longitudinally remote from the transverse centerline T. Line N should be parallel to the transverse centerline. If the line N is viewed as being the end line of the insert 44, then the end edge 44D of the insert 44 can be thought of as having at least two gaps (indentations, or recessed areas) 72 along the end line, N, of the insert 44. These gaps 72 can also be in any suitable configuration. Suitable configurations include, but are not limited to, slits (shown in FIG. 6A) and notches, including trangular-shaped notches, and the preferred curved indentations shown in FIG. 1.

FIG. 1 shows one preferred configuration in which the end line of the insert N, runs between the wing tips 70 of the insert. It should be understood that this is a preferred configuration, and that other configurations are also possible. For example, in other alternative embodiments, the hump portion 66 of the end edge 44D may project further outward from the transverse centerline than the wing tips 70. In such a case, end line, N, would run through the apex of the hump portion 66.

The gaps 72 along the end line of the insert 44 are preferably located between the central body 46 of the insert and the wings 48 of the insert (in other words, the gaps 72 are located in the area of the longitudinal edges 58 of the central body 46). The gaps 72 are, thus, typically located in the region where the insert 44 changes from a convex upward curvature to a concave upward curvature. The location of the gaps 72, however, is not confined to the longitudinal edges 58 of the central body 46 of the insert 44. The gaps 72 can be located in these areas as well as in the surrounding areas, including, but not limited to the transition regions 59. The importance of the location of the gaps 72 is described below (in conjunction with the discussion of the dynamic in-use characteristics of the insert).

FIG. 1 shows that the insert 44 is preferably positioned in the central region 32 of the sanitary napkin. The insert 44 may be located above the absorbent core 42, below the core (as shown in FIG. 4), or within the core (and can, thus, be considered part of the core) of the sanitary napkin 20. The resilient insert 44 may be liquid pervious, semi-pervious, or liquid impervious (if it lies beneath the absorbent core 42), absorbent or nonabsorbent, with a preferred embodiment being absorbent. Thus, in the preferred embodiment when the insert is absorbent, the insert 44 can provide additional absorbent capacity in the central region of the sanitary napkin 20 where it is needed most. In addition, although the insert 44 is shown as having a length that is only a portion of the length of the sanitary napkin, in other embodiments, the insert 44 can be made up to the full length of the sanitary napkin and can comprise substantially all of the absorbent material in the sanitary napkin so that the insert 44, in effect, serves as the absorbent core of the sanitary napkin 20.

Figure 8:
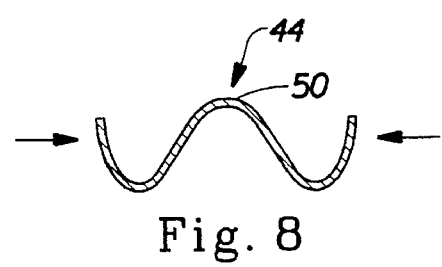
FIG. 8 is a cross-sectional view of the insert of the sanitary napkin shown in FIG. 4 in an in-use configuration.

The resilient insert 44 may be of any caliper. However the caliper of the insert 44 is preferably less than or equal to about 1.25 mm, more preferably less than about 1 mm or less, so that the total caliper of the sanitary napkin 20 is no greater than about 3 mm. It is understood, however, that thicker inserts and thicker sanitary napkins can also be provided within the scope of the invention. It should also be understood that the various calipers referred to herein are measured as shown in FIG. 8 from one point on one surface of the article or element in issue to the nearest point on the opposed surface of the article or element (that is, rather than between a plane that passes through the uppermost portion(s) of the insert and a plane which passes through the lowermost portion(s) of the insert). FIG. 8 shows the proper way to measure the caliper, C, of the insert.

The central arcuate portion 50 (or central body 46) of the insert 44 preferably ranges in length from about 25 mm to about 125 mm as measured along the longitudinal centerline. In a particularly preferred embodiment, the central arcuate portion 50 is about 85 mm long. The overall width of the insert 44 can range up to 80 mm, or more. The overall width of the insert 44 is preferably about 2 ¼ inches (about 5.7 cm) at its narrowest portion. The central arcuate portion 50 preferably ranges in width from about 5 mm to about 80 mm, and in a particularly preferred embodiment is about 40 mm wide. The central arcuate portion 50 preferably ranges in height up to about 20 mm, and in a particularly preferred embodiment the central arcuate portion 50 has a height of about ½ inch (about 10 mm to about 13 mm). These width and height measurements may also establish ranges for the radius of curvature of the central arcuate portion 50. In addition, the radius of curvature of the central arcuate portion 50 can be greater than the height of the central arcuate portion (so that the central arcuate portion defines a flatter curve). In one preferred embodiment, for example, the central arcuate portion 50 has a radius of curvature of about 24 mm.

It should be understood that it is also within the scope of the present invention for the body-conforming component to be flat so that its central body 46 and lateral side portions 48 do not initially define any type of an arcuate structure. The initial height of these portions of such a component will essentially be zero. When the sanitary napkin is compressed, the different portions of the body-conforming component can preferably bend into arcuate shapes which have dimensions in the ranges described above. Further, since the body-conforming component is capable of dynamically adjusting in use to conform to the wearer's body, it should be understood that the dimensions of the body-conforming component preferably vary within the specified ranges with the wearer's body movements.

The lateral arcuate portions 52 and 54 preferably range in length from about 25 mm to about 270 mm. In a particularly preferred embodiment, the lateral arcuate portions 52 and 54 are about 125 mm long. The lateral arcuate portions 52 and 54 preferably have a width that is between about 5 mm and about 40 mm. The radius of curvature of the lateral arcuate portions 52 and 54 preferably ranges from about 1 mm to about 5 mm, and preferably is about 3 mm.

The resilient insert 44, as noted above, is intended to form a rounded W-shaped cross-sectional configuration in use. The insert 44 preferably changes its cross-sectional configuration prior to compression by the wearer's thighs from that shown in FIG. 4 to the more pronounced W-shaped cross-sectional configuration shown in FIG. 8 when compressed by the wearer's thighs. The cross-section of the insert 44 shown in FIG. 8 is formed when the central arcuate portion 50 of the insert assumes a more narrow (i.e., smaller radius of curvature) convex upward configuration and the lateral arcuate portions 52 and 54 assume more narrow concave upward configurations.

The multiple arcuate cross-sectional shape of the insert 44 provides several advantages. Many of these advantages involve comfort and fit of the sanitary napkin. The fact that the insert 44 comprises a smooth curve which is free of hinge lines is believed to provide a more comfortable sanitary napkin for the wearer.

The use of arcuate sections rather than hinge lines is also believed to provide the sanitary napkin with a greater ability to adjust wearer's of various sizes and to more comfortably self-adjust in the event the sanitary napkin is not properly initially positioned/applied against the wearer's body.

The fact that the insert 44 is comprised of a continuous assembly of arcuate portions uninterrupted by hinge lines is believed to provide the insert with greater resiliency when subjected to lateral compression. Arcuate structures are generally more resistant to lateral compression and more resilient after being subjected to lateral compression than are hinged structures due to the absence of hinges since hinges dissipate much of the applied compressive forces. This characteristic allows a resilient structure to be created out of thinner materials and out of materials that have less inherent resiliency than hinged structures.

Figure 9:
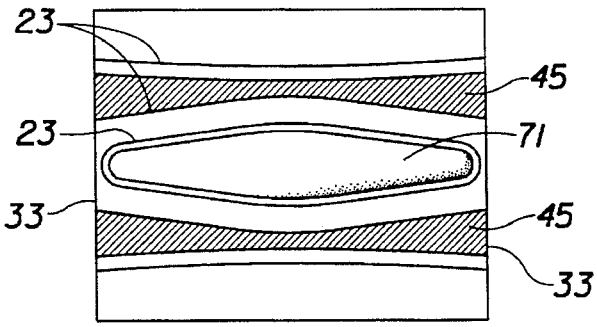
FIG. 9 is a plan view of a prior art insert.

The butterfly plan view shape of the resilient insert 44 serves at least two main purposes. The butterfly shape facilitates the formation of the desired "W"-shaped cross-section in the central region 32 of the sanitary napkin 20. This occurs because the insert 44 does not have any constraining material between the arcuate portions that tend to resist the ability of the insert to form into the desired W-shaped cross-sectional configuration. This can be contrasted with the insert shown in FIG. 9. FIG. 9 shows an example of a prior art flexure-resistant deformation element in the form of an insert which has flexure means such as flexure hinges 23, a protruberance 71, and constraining material 45 between those sections of the insert which are intended to bend in different directions during use. The constraining material 45 is shaded in FIG. 9. The butterfly-shaped insert 44 of the present invention differs from this insert in that it does not have constraining material between sections that bend in different directions. This allows one section of the insert (such as the central body) to bend one way (convex upward) and other sections (such as the wings) to bend the opposite way (concave upward) with greater ease.

The butterfly shape also aids the end regions 28 and 30 of the sanitary napkin in assuming the desired shapes in use. FIGS. 8 and 10–12 show that the sanitary napkin 20 preferably takes a number of different cross-sectional configurations when it is worn depending on the place along the length of the sanitary napkin 20 through which cross-sections are taken. The sanitary napkin 20 preferably adapts to the three very distinct shapes of the wearer's body. From the front of the wearer's body, the first of the three regions may be thought of as the mons region, M, which, as shown in FIG. 11, has a curved convex shape. The second region is defined by the labia majora and resembles a W-shaped outline. The third region is determined by the crevice between the wearer's buttocks (or the "gluteal groove", G) and is generally cusp-shaped and defined by two convex and outwardly diverging lines.

FIG. 11 is a schematic cross-sectional view showing the way the first end region 28 of the sanitary napkin of the present invention might fit adjacent the wearer's mons region, M. The cross-sectional configuration of the central region 32 of the sanitary napkin is preferably similar to the cross-sectional configuration W-shape cross-sectional configuration of the insert shown previously in FIG. 8. FIG. 12 is a schematic cross-sectional view showing the way the second end region 30 of the sanitary napkin of the present invention might fit in the crevice between the wearer's buttocks ("gluteal groove") G. The central arcuate portion 50 assists the second end region 30 of the sanitary napkin in forming such a shape. This occurs because the bending of the sanitary napkin into the inverted U-shape or inverted V-shape cross-sectional shape by the central arcuate portion 50 often extends into the second end region 30 of the napkin which is retained in the second end region 30 due to the shape of the wearer's gluteal groove.

The central projections (or hump portions) 66 of the W-shaped plan view of the insert 44 provide extensions that also serve several particular purposes. The central projections 66, as noted above, are those portions of the central body 46 of the insert 44 that extend from the base of the W-shape defined by the end edges 44D of the insert to form the ends of the central body 46 of the butterfly-shape. These central projections 66 are designed to be easier to bend downward than the portion of the insert in the central arcuate portion 50 that forms a hump. The extensions are also more easily compressed laterally due to their lesser width. These features are important because the central projections 66 are generally the portions of the insert 44 which are closest to the wearer's clitoris at one end and wearer's anus at the other end. The ease with which the central projections 66 can bend and compress reduces any tendency for the resilient insert to irritate these sensitive areas of the wearer's body.

The tapering of the central body 46 of the insert 44 into the end extensions also provides the sanitary napkin with a more gradual transition in flexibility between the central region 32 of the sanitary napkin and the end regions 28 and 30. The sanitary napkin 20 (as described in greater detail below) preferably has end regions 28 and 30 that are highly flexible. This gradual transition in flexibility differs from the type of transition in flexibility provided by many prior types of inserts. For example, FIG. 9 shows an insert which has "squared-off" end edges 33. If the insert shown in FIG. 9 is relatively stiff, the sanitary napkin will tend to form bending axes that run transversely across the sanitary napkin at the ends 33 of the insert. This may present a sanitary napkin with a relatively abrupt transition in flexibility along the length of the sanitary napkin. The shape of the ends of the insert 44 of the present invention, on the other hand, tends to provide the sanitary napkin with a more smooth transition in flexibility between the different regions of the sanitary napkin since the end edges 44D of the insert 44 are tapered as the end regions of the napkin are approached.

Overall the resilient insert 44 should preferably be relatively flexible. The flexibility of the insert 44 should be enough that the sanitary napkin is comfortable to wear. The flexibility of the insert 44 is not unlimited, however, since the insert 44 must resist flexibility enough to maintain the sanitary napkin in the desired in use configurations without collapsing under the forces associated with wearing the napkin. The insert 44 is preferably flexure-resistant, reformable, and moisture stable as these terms are defined in the U.S. Pat. No. 5,171,302 issued to Buell. The insert 44 and the sanitary napkin may also be made to assume many of the cross-sectional configurations described in the aforementioned patent. However, it is understood that the insert 44 of the present invention is of an improved configuration over the inserts described in the Buell patent. More particularly, the insert described herein has an improved structure which is designed to achieve the desired in-use configurations even more efficiently in thinner, more consumer-friendly exeuctions due to its butterfly plan view shape and multiple arcuate cross-sectional configuration.

The insert 44 should be laterally compressible under relatively low forces so that the sanitary napkin is comfortable to wear. When worn, sanitary napkins and other related catamenial products are subjected to lateral compression forces. The insert 44 should be resilient enough that the sanitary napkin should preferably return to its uncompressed state when these compressive forces are released. This ensures that the insert 44 will enable the sanitary napkin 20 to cover a large portion of the wearer's panties during use and to minimize lateral leakage of exudates around the sides of the sanitary napkin which leads to staining of the wearer's panties (which may be referred to as "side soiling"). The manner in which the sanitary napkin reacts to these compressive forces is also important since it affects the visual appearance of the sanitary napkin after use.

The compressive forces are preferably measured as the amount of force necessary to hold the central portion of the sanitary napkin compressed in the cross direction (i.e., width) in both the dry and wet states. The resiliency of the sanitary napkin can be measured as both the percent recovery of the initial width of the sanitary napkin and the absolute width recovered in the central portion of the sanitary napkin after it has been subjected to cross-directional compression. The absolute width recovered after compression relates to the ability of the sanitary napkin to sufficiently cover the panty to protect it from soiling. The percent recovery of the sanitary napkin after compression has been found to correlate to the visual appearance of the product after use. For example, in the latter case, sanitary napkin users have evaluated sanitary napkins that have considerably narrower widths at the time of removal (relative to the sanitary napkin before it is worn) as being poorly performing due to their perception of their tendency to bunch.

Although compressive forces and recoveries are measured in both the dry and wet states, many of the wearer's perceptions as to comfort appear to be formulated as the sanitary napkin is first being worn. This means that compressive forces and recoveries in the dry state may be more relevant to the wearer's perceptions of comfort than are those in the wet state. It has been found that thin sanitary napkins having compressive force values of about 300 g or less, preferably about 200 g or less, in the dry state are considered to be comfortable when worn. Preferably, sanitary napkins according to the present invention have compressive force values in the dry state in the range of from about 50 to about 300 g, and more typically from about 100 to about 200 g.

Most sanitary napkins suffer a loss in their properties for recovery as they become wet. This means the wet state of the sanitary napkin is more critical to sustained area coverage of the panty than is the dry state. Sanitary napkins which have an absolute width after wet compression of at least about 48 mm (preferably, at least about 55 mm) sufficiently cover the panty area to have an impact on the prevention of panty soiling. Preferably, sanitary napkins according to the present invention have a width (or compression recovery value) at the center after wet compression in the range of from about 48 to about 70 mm, and are more typically in the range of from about 55 to about 65 mm.

Similarly, since many sanitary napkin users make a visual assessment of the sanitary napkin after it has been worn for a period of time (i.e., when checking or removing the sanitary napkin), the sanitary napkin is more than likely to contain some amount of liquid body exudates. Thus, the wet state is important to the visual appearance of the product after use. Sanitary napkins which recover (at the center) from the wet compressed state at least about 65% (preferably at least about 75%) of their initial width appeal to catamenial users for their visual appearance after use. Sanitary napkins according to the present invention preferably recover after wet compression from about 55 to about 90% (more typically from about 75 to about 85%) of the initial sanitary napkin width.

The procedure for measuring the compressive force values on an absorbent article in the dry state, and the absolute and relative recovery from compression (i.e., resiliency) in the wet state are set forth in the Test Methods section of this specification.

The insert 44 can be formed from many of the types of materials used in the various components of the sanitary napkin (such as the types of materials used in the absorbent core, as the backsheet, or combinations thereof). For instance, the insert 44 can be formed from absorbent material such as webs or laminates of absorbent material (with or without absorbent gelling materials). Examples of suitable absorbent materials include webs of cross-linked cellulosic fibers and meltblown webs. Alternatively, the insert can be made from impervious materials. Examples of some suitable nonabsorbent materials include thermoplastic polyethylene, polypropylene, synthetic foams, films or suitable blends of the types of materials described herein. One preferred foam material for use in the insert is a polyethylene foam known as VOLARA 2a obtained from Voltek Corp., Lawrence, Mass. It is preferred, however, to form the insert from an absorbent material, and a material such as a thermally bonded airlaid web (which may be referred to herein as "TBAL" for brevity) that has some resiliency.

The insert 44 preferably contains at least some thermoplastic material. The use of thermoplastic material has the advantage that upon melting, at least a portion of the thermoplastic material migrates to the intersections of the fibers, typically due to interfiber capillary gradients. These intersections become bond sites for the thermoplastic material. When cooled, the thermoplastic material at these intersections solidifies to form the bond sites that hold the web or matrix of fibers. Bonding at these fiber intersections increases the overall compressive modulus and strength of the resulting matrix. Preferably, the insert 44 comprises a matrix that contains from about 10 to 90% cellulosic fibers and from about 10 to about 90% thermoplastic fibers or material.

In a particularly preferred embodiment, the resilient insert 44 is made of a thermally bonded absorbent material fabricated from a blend of cellulose and synthetic fibers. Such a preferred material for the insert 44 is described in the aforementioned U.S. patent application Ser. No. 08/141,156, entitled, "Catamenial Absorbent Structures Having Thermally Bonded Layers for Improved Handling of Menstrual Fluids, and Their Use in Sanitary Napkins Having Improved Fit and Comfort" filed in the name of Richards, et al. on Oct. 21, 1993. Such a material is preferred because, unlike many foam materials, it is absorbent, and it has inherent resiliency, and it can be formed into resilient strucuetures without having cells that are crushed in the process (which often happens with foam materials).

Such particularly preferred thermally bonded absorbent material is obtained as DANWEB material #'s 1079–2338 and 1079–2339 from Dan Web of Aarhus, Denmark. DANWEB material #1079–2338 comprises a homogeneous blend of about 70% Flint River fluff (cellulose), 15% DANAKLON ES-C 1.7 dtex×6 mm bicomponent fibers, and about 15% Nalco 1180 absorbent gelling material particles. DANWEB material #1079–2338 is formed into a web having a basis weight of about 152 grams/m², a caliper of about 1.2 mm measured under a load of 0.2 psi, and a density of about 0.13 g/cc. DANWEB material #1079–2339 comprises a two layer composite wherein the layers are thermally bonded and densified. The first layer has the same composition as material #1079–2338. The second layer comprises a homogeneous blend of about 85% Flint River fluff and 15% DANAKLON ES-C 1.7 dtex×6 mm bicomponent fibers. The composite web has a basis weight of about 290 grams/m², a caliper of about 2.3 mm, and a density of about 0.13 g/cc.

The resilient insert 44 can also comprise a laminate of a thermally bonded absorbent material and other materials. One particularly preferred laminate comprises a laminate of DANWEB #1079–2338 material and one or more layers of an 18 g/yd² (21.5 g/m²) spunbonded polypropylene nonwoven material known as CELESTRA available from Fiberweb, North America of Simpsonville, S.C., which is then embossed with the pattern described in U.S. Pat. No. 4,781, 710 issued to Megison, et al. on Nov. 1, 1988, and referred to internally at P&G as P-9. Both layers of P-9 material are preferably melted to the back of the DANWEB material.

The thermally bonded airlaid material can be formed by metering an airflow containing the fibers and thermoplastic material, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. U.S. Pat. No. 31,775; U.S. Pat. No. 4,278,113 (Persson), issued Jul. 14, 1981; U.S. Pat. No. 4,264,289 (Day), issued Apr. 28, 1981; U.S. Pat. No. 4,352, 649 (Jacobsen et al), issued Oct. 5, 1982; U.S. Pat. No. 4,353,687 (Hosler, et al), issued Oct. 12, 1982; U.S. Pat. No. 4,494,278 (Kroyer, et al), issued Jan. 22, 1985; U.S. Pat. No. 4,627,806 (Johnson), issued Dec. 9, 1986; U.S. Pat. No. 4,650,409 (Nistri, et al), issued Mar. 17, 1987; and U.S. Pat. No. 4,724,980 (Farley), issued Feb. 16, 1988. A particularly desirable system for air-laying mixtures of fibers and thermoplastic material according to the present invention is disclosed in U.S. Pat. No. 4,640,810 (Laursen et al), issued Feb. 3, 1987.

The resilient insert 44 can be formed at the same time as the absorbent core 42, or it can be made separately from the absorbent core. In the former case, the insert 44 can either be made as a separate component, or it can be made integrally with the absorbent core.

The following will describe one preferred non-limiting way of making a curved resilient insert from thermally bonded airlaid material and a sanitary napkin as shown in FIGS. 1–5 with such an insert that lies below the absorbent core. In the sanitary napkin described below (though inserts located below the core can be non-absorbent), an absorbent insert will be employed.

The components of the insert are obtained. The components used in this method comprise two plies of the P-9 spunbonded polypropylene nonwoven material described above and a single web of thermally bonded air laid ("TBAL") material product #1079–2338 obtained from Dan Web of Aahus, Denmark. The components should be larger in size than the final size of the insert desired.

The equipment needed to form the insert 44 includes an iron capable of heating to about 300° F., a die (preferably in the form of a wire screen), a template, and a vacuum former. An example of one suitable vacuum former is shown in FIG. 13. The vacuum former 100 can be a vacuum former suitable for making blister packages such as a QVac machine obtained from QVac of Santa Fe Springs, Calif. The vacuum former 100 comprises a base 104, a heat source 108, a wire screen 110, and a vacuum source 112. The vacuum former 100 is preferably also provided with a plunger 114 having a pair of curved projections 116.

The two plies of P-9 material are placed over the TBAL material. Two plies are used to give the insert the desired stiffness. The P-9 material is covered with a sheet of TEFLON to keep the iron from sticking to the P-9 material. The iron is run over the TEFLON to melt the P-9 material onto the TBAL web. Melting of the P-9 material makes the P-9 nonwoven material form into an air impervious (and liquid impervious) film, insert blank 44'. This imperviousness to air is used to draw a vacuum against the insert blank 44' to vacuum-form the insert.

The insert blank 44' is placed in the vacuum former 100 on top of the wire screen 110. The wire screen 110 essentially comprises a three-dimensional die through which the vacuum is drawn to shape the insert blank 44'. The wire screen 110 is preferably placed face up over the vacuum source so that the convex central portion 118 is convex upward. The insert blank 44' is then draped over the wire screen 110. The edges of the insert blank are taped to the surface of the base 104 of the vacuum former 100 so air will not be able to enter underneath the edges of the insert blank 44'.

The vacuum former 100 is pre-heated until it reaches about 650° F. The heat source 108 is then brought down over the insert blank 44' to heat the insert blank 44' so it will be pliable enough to be drawn against the wire screen by the vacuum. Heat is applied for about 25 seconds. During the heating phase, the plunger 114 is brought down so the curved projections 116 press down slightly on the insert blank 44' and portions of the insert blank 44' more into the curved recessed areas 120 in the wire screen 110. This ensures that the insert blank 44' fits closely to the mold in these regions. About four seconds before reaching the end of the 25 second heating phase, the vacuum is applied. The vacuum is applied for about 10 seconds. After the vacuum is applied, a fan cools the pre-formed insert 44" formed thereby. The pre-formed insert 44" is then cut to the desired size using the butterfly-shaped template. The template is sized to cut the pre-formed insert 44" along lines that correspond to the ridges 122 on the wire screen 110 and along W-shaped lines at the end edges of the pre-formed insert. The formation of the insert 44 is now complete.

It should be understood that vacuum forming of the insert is only one preferred way of forming the insert. A suitable insert can be formed by molding, shaping, or by any of the other means described in U.S. Pat. Nos. 5,171,302 and 5,197,959 issued to Buell. Vacuum forming is preferred, however, because it does not generally create densified regions in the insert. (Although the portions of the insert that were contacted with the curved projections of the plunger may be slightly densified). This provides the insert 44 with improved overall resiliency since hinge points in the form of creases, and the like, will not be created. It also avoids compressing the absorbent TBAL material so that the inter-fiber spacing of the same is not affected. Thus, the good absorbent properties of the TBAL material remain unaffected and relatively uniform over the entire insert.

The assembly of the sanitary napkin using the insert described above is as follows. A web of the same type of TBAL material (#2338) is cut in the configuration of the absorbent core. The completed insert 44 is tightly glued to the underside of the web of TBAL used for the absorbent core. Preferably, the glue is applied in a spray or spiral pattern that is pervious so that it permits liquids to transfer through the core 42 to the insert 44. A sheet of polyethylene film is then cut to the shape of the backsheet. Tape is applied around only the central body portion 46 of the insert 44. The insert 44 with the overlying core material attached, is then joined to the backsheet using the tape around the perimeter of the central body portion 46 of the insert 44. This ensures that the insert 44 will not be bonded to the backsheet over its entire bottom surface. This allows for some decoupling between the insert 44 and the backsheet 40. (The concept of decoupling is described in greater detail in U.S. Pat. No. 5,007,906 issued to Osborn, et al. on Apr. 16, 1991.) A web of apertured formed film is cut in the shape desired for the topsheet for placing the same over the composite of the absorbent core, insert, and backsheet. The face of the topsheet is bonded to the face of the absorbent core by one (or more) of the bonding methods described herein. The topsheet is then peripherally bonded to the backsheet by adhering, crimping, or the like. A panty fastener is applied to the backsheet. The body-facing side of the topsheet is then sprayed with a surfactant to complete the assembly of the sanitary napkin.

Numerous variations of this process are also possible. For instance, different or additional components of the sanitary napkin can be vacuum formed as described above. In still other embodiments, the entire sanitary napkin can be vacuum formed after its components have been assembled. In other versions of this process, the vacuum forming of the various components of the sanitary napkin can be carried out by drawing a vacuum against a semi-air pervious component. Alternately, air pervious components can be used so long as the vacuum pressure differential applied to the component(s) of the sanitary napkin that are being vacuum formed is great enough to draw such component(s) against the vacuum forming die. In addition, in vacuum forming the entire sanitary napkin, a screen similar to that described above can be used which is curved. The screen can be as long as the sanitary napkin, and the entire sanitary napkin can also be vacuum formed in a curved configuration from back to front, or in any other suitable manner.

(2) Flat Inserts

Figure 7:
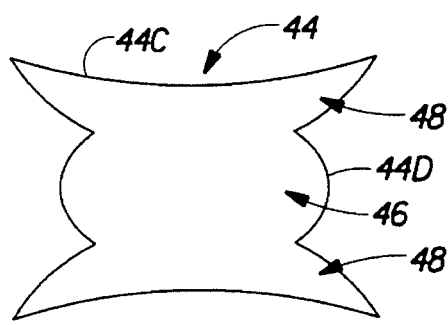
FIG. 7 is a plan view of a flat insert.

The resilient insert 44 can, alternatively, be relatively flat as shown in FIG. 7. In such a case, the arcuate portions can be omitted from the insert 44 and a substantially two-dimensional insert 44 can be provided in the plan view shape shown in FIG. 1 (or some suitable variation thereof). Such an insert can be formed by simply cutting a piece of (preferably resilient) material to the desired shape. Flat inserts are particularly preferred for use in ultra thin sanitary napkins (i.e. caliper less than about 3 mm) because they can provide the sanitary napkin with the desired in-use configuration without substantially adding to the thickness of the napkin.

The insert 44 is preferably provided with deformation lines to assist it in assuming the desired shape in use. Both flat and curved three-dimensional inserts may be provided with deformation lines, deformation dots (or areas of deformation having other configurations) to assist the inserts in assuming the desired shape in use. Deformation lines, 80 (examples of which are provided on flat inserts shown in FIGS. 15A–18B), however, are typically more essential for inserts that are formed flat and must be bent into the desired configuration during use. The flat inserts preferably assume a shape in use which is as close as possible to the shape of the curved inserts having multiple arcuate portions of the described previously.

(3) Alternative Insert Configurations

FIGS. 15A–21B show several sanitary napkins having alternative insert configurations and the cross-sectional shapes the inserts assume in use.

FIG. 15A shows a sanitary napkin having a flat insert with a hexagonal shape. The length of the two sides of the hexagon-shaped insert that are oriented in the longitudinal direction are longer than the other sides. The sides of the insert that are oriented in the longitudinal direction are preferably about twice the length of the other sides. The hexagonal-shaped insert is provided with a longitudinally-oriented groove 78 on its garment-facing side. The groove 78 only passes part of the way through the thickness of the insert. Although the groove 78 is hidden from view in FIG. 15A, and therefore should be represented by a dashed line, it is shown as a solid line to differentiate it from the embodiments having embossed deformation lines shown in the figures which follow. FIG. 15B shows the inverted V-shaped cross-sectional configuration such an insert takes when the sanitary napkin is compressed in use.

FIG. 16A shows a sanitary napkin with an insert 44 having a hexagonal shape and a central longitudinally-oriented embossed line (or "compression line") 80A formed on the underside of the insert. The central longitudinally-oriented compression line 80A assists the center of the insert in folding into a convex-upward configuration when compressed. This compression line is shown as a dashed line in FIG. 16A because it is hidden from view. This compression line may be a continuous line. FIG. 16B shows the inverted "V"-shape with a rounded apex cross-sectional configuration this insert takes in use. It should be understood that the present invention is not limited to embodiments having continuous compression lines (or grooves), and that any of the compression lines (or grooves) shown in these figures can be intermittent. It should also be understood that any of the inserts described herein that are provided with single compression lines (or grooves) in a given region of the insert can be provided with multiple compression lines (and/or grooves) in such regions. Multiple compression lines (or grooves) are particularly useful if it is desirable to provide an insert with a tendency to form a more rounded folded structure. These multiple compression lines (or grooves) may be oriented in the same direction. If the compression lines (or grooves) are oriented in the same direction, they may be substantially parallel, but it is also possible to create embodiments where they are not parallel.

FIG. 17A shows a sanitary napkin with a flat insert 44 having a hexagonal center ("central body") with small wings. The insert shown in FIG. 17A is provided with a central longitudinally-oriented compression line 80A embossed on the underside of the hexagonal portion of the insert similar to the insert shown in FIG. 16A. The insert shown in FIG. 17A, however, is also provided with two longitudinally-oriented compression lines 80B between the central body 46 and the wings 48 that are embossed into the body-facing side of the insert to assist the wings 48 in folding upward. FIG. 17B shows the shape this insert forms during use and the barriers formed by the wings 48 of the insert.

FIG. 18A shows a sanitary napkin with an insert 44 having a hexagonal center with wider wings (as measured in the transverse direction) and compression lines similar to those shown in FIG. 17A. FIG. 18B shows that this insert forms a W-shape with more pronounced (or longer) legs.

FIG. 19A shows a sanitary napkin with an insert 44 that has a hexagonal center 46 similar to the insert shown in FIG. 18A. The hexagonal center of the insert 44 shown in FIG. 19A, however, is provided with an arcuate cross-section. FIG. 19B shows the cross-sectional configuration such an insert takes in use.

FIGS. 20A and 20B show the preferred pre-formed insert shown in FIGS. 1–5 and the rounded "W"-shape configuration it takes in use.

FIGS. 21A and 21B show a sanitary napkin with an "X"-shaped (or "X-cut") flat insert 44 that is preferred for use in thicker sanitary napkins (e.g., greater than or equal to about 5 mm thick) and the boat-like cross-sectional configuration it takes in use. The X-cut insert provides these thicker sanitary napkins with sides that stand up when the napkin is compressed by the wearer's thighs. The central portion of the X-cut insert does not require the features of the inserts shown above (e.g., thinness, arcuate central body, extensions at the ends of the central body) because the lateral compression of the sanitary napkin together with the extra absorbent material found in thick sanitary napkins should cause the portion of the sanitary napkin along the longitudinal centerline L to bulge upward without providing the x-cut insert with these features.

The inserts shown in FIGS. 15A–20B can be thought of as representing a gradual evolution from the most basic inserts (FIG. 15A) to the more preferred inserts (FIGS. 19A and 20A). The inserts shown as being earliest in the evolution (FIGS. 15A and 16A) can deform to provide a raised center portion, but do not provide the desired W-shape cross-section use which allows the sanitary napkin to both form barriers and to provide maximum area coverage at the insides of the wearer's thighs. The rounding of the cross-sectional shape of the more preferred inserts provides improved comfort and allows the sanitary napkin to more readily adjust in position relative to the wearer's body and if the sanitary napkin is inadvertently misapplied, etc. (for example, if the sanitary napkin is not placed exactly along the centerline of the wearer's body).

(4) Selective Stiffeners

The body-conforming portion or component of the present invention can alternatively comprise a selective stiffener. The term "selective stiffener", as used herein, refers to a portion or component of the sanitary napkin with regions that have different stiffnesses. The selective stiffener has at least one region (e.g. a first region) that is stiffer than one other region (e.g., a second region). These regions are used to assist the component in bending into certain desired configurations. The component will generally bend about its less stiff second regions.

FIG. 22 shows an example of a body-conforming component that is provided in the form a selective stiffener 82. The selective stiffener 82 includes stiffened first regions 84 and second unstiffened (or less stiffened) regions 86. The selective stiffener 82 shown in FIG. 22 has a pattern of stiffened first regions 84 that are in a form similar to the butterfly shape of the inserts described previously. The selective stiffener 82 is intended to bend about the more flexible second regions 86 and deform into the same shape as the inserts described previously.

The selective stiffener 82 shown in FIG. 22 can be formed in a number of ways. A non-limiting number of these ways are as follows. Preferably, these ways utilize a base material (i.e., starting material) within which material thermal bonds can be formed, or to which material other materials can be thermally bonded. Most preferably, such methods use a thermally bondable absorbent material such as the preferred TBAL materials described above. The selective stiffener 82 can be formed of a base material comprising a separate component, or the base material may comprise the topsheet, backsheet, or absorbent core.

One preferred way of creating stiffened regions 84 is by heating selected regions of the thermally bondable material without applying pressure to the material. This can be done, for example, by covering the base material with a template and heating the base material with a hot air gun.

Another way of creating stiffened regions is by attaching a stiffening material to selected portions of the base material. In a preferred embodiment of this method, a thermoplastic material is used for the stiffening material, and the thermoplastic stiffening material is melted onto one side of the base material by heating the thermoplastic stiffening material.

Several advantages are provided by the selective stiffeners. One primary advantage is that selective stiffeners can be created that are very thin yet are capable of assuming in-use configurations similar to those of the curved inserts described above. This is of particular interest for ultra-thin absorbent articles. In addition, a component of the sanitary napkin such as the absorbent core can be formed into a selective stiffener. This has the advantage of eliminating the need to add a separate component to the sanitary napkin and avoids the associated material and processing costs. Another primary advantage of selective stiffeners is that if pressure is not applied during the process of making the selective stiffener, the stiffened regions will not be densified to any significant extent. This is particularly important if it is desired to create a selective stiffener out of absorbent material in such a manner that the absorbency and wicking properties are not affected by the creation of the stiffened regions. The selective stiffener can, thus, be provided with uniform absorbent and wicking properties over its entire surface.

E. Combinations of Topsheet, Backsheet, and Core Materials and Assembly of the Same Into a Sanitary Napkin.

The components of the sanitary napkin described above (the topsheet, backsheet, and absorbent core) can be assembled in any suitable manner.

In the preferred embodiment shown in FIGS. 1–5, the components of the sanitary napkin are assembled in a "sandwich" configuration with the components sized so that the edges of the topsheet 38 and backsheet 40 extend outward beyond the edges of the absorbent core 42. The topsheet 38 and backsheet 40 are preferably at least partially peripherally joined using known techniques.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The components of the sanitary napkin 20 can be joined together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, extruding one component onto another, or by any other means known in the art. Suitable means for attaching the components of the sanitary napkin are described in U.S. patent application Ser. No. 07/944,764 filed in the name of Cree, et al. on Sep. 14, 1992, and continuations thereof (PCT Publication No. WO 93/11725 published Jun. 24, 1993). As shown in FIG. 1, the topsheet 38 is preferably secured to backsheet 40 along a liquid impervious seam 90. The seam 90 can be formed by any means commonly used in the art for this purpose such as by gluing, crimping, or heat-sealing.

The sanitary napkin 20 of the present invention can also be comprised of different combinations of the topsheet, backsheet, and core materials. The sanitary napkin 20 may, for example, be comprised of all extensible components. The sanitary napkin 20 may also be comprised of any of the types or combinations of extensible or inextensible topsheets, backsheets, and absorbent cores that are described in U.S. patent application Ser. No. 07/915,133, filed Jul. 23, 1992, in the name of Osborn, et al. (PCT Publication No. WO 93/01785).

When the sanitary napkin 20 is comprised of extensible components, the components can be joined together in any suitable manner that allows the sanitary napkin to extend. In one preferred example of such a structure, the backsheet 40 comprises a stretchable adhesive film. The core 42 is placed between the topsheet 38 and the backsheet 40. The portions of the edges of the topsheet 38 that extend outward beyond the edges of the core 38 are secured to the corresponding portions of the backsheet 40 using the adhesive backsheet film disposed around the perimeter of the absorbent core. It has been found that such a construction adequately secures the components of the sanitary napkin without further securing the faces of the adjacent components to each other. Although, as noted above, it is often preferred to secure some of the components at their faces, as well.

The above manners of joining the components are preferred for ease of construction. (Other means of uniting the various components can be used.) For instance, the present invention also includes so-called "tube" products. In these products, a liquid pervious cover material (such as topsheet material) can be wrapped completely around the absorbent core and the backsheet, and then the components can be secured together. In alternative arrangements, the topsheet could be wrapped around the core, and the wrapped core could be placed on and secured to the backsheet.

F. Additional Alternative Embodiments and Features

The sanitary napkin may have various alternative embodiments and/or features. One preferred alternative embodiment is to combine the insert in a sanitary napkin with additional design features to aid the center lift such as a garment-facing side with a concave portion as shown in FIG. 2 or the decoupled cores described in U.S. Pat. No. 5,007,906 issued to Osborn, et. al. on Apr.6, 1991.

Figure 23:
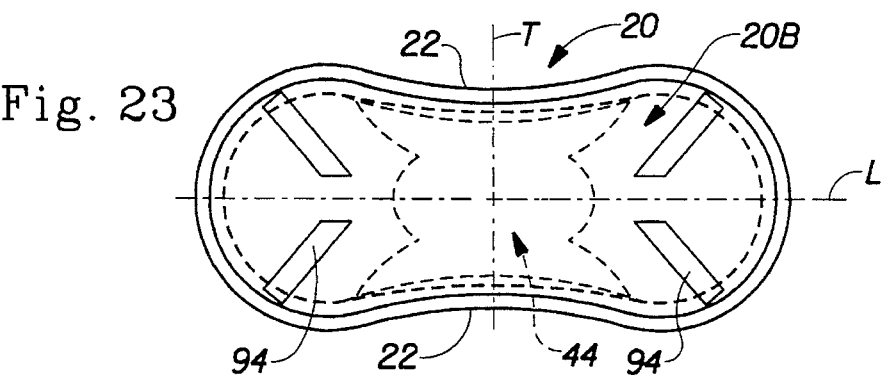
FIG. 23 is a plan view of the garment-facing side of a sanitary napkin according to the present invention which shows a preferred adhesive fastener pattern.

FIG. 23 shows that in other alternative embodiments, the sanitary napkin 20 can be provided with a modified V-shaped panty fastener pattern related to that described in U.S. patent application Ser. No. 07/915,201, filed Jul. 23, 1992, in the names of Olsen, et al., and its corresponding international application, PCT Publication No. WO 93/10783 published Feb. 4, 1993. Such a panty fastener can comprise an adhesive or any other type of fastener known in the art as being suitable for such a purpose. Such a fastener pattern allows portions of the sanitary napkin both along the longitudinal centerline and the transverse centerline to decouple from the wearer's panties. This provides a sanitary napkin that conforms more easily to the wearer's mons region, introitus, and gluteal groove.

Figure 24:
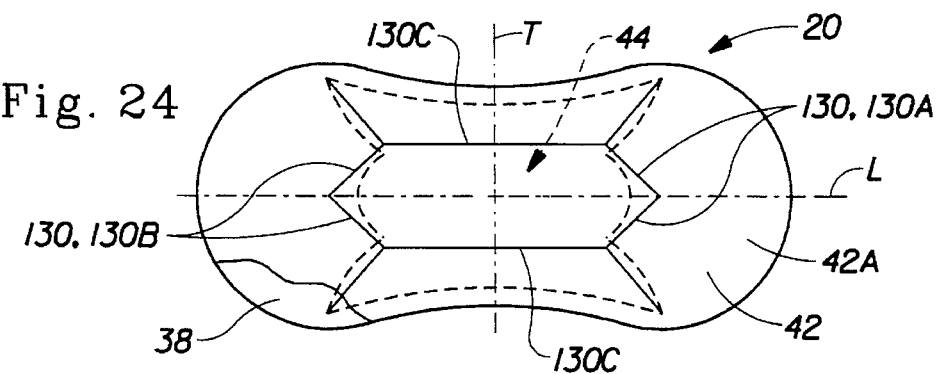
FIG. 24 is a plan view of the body-facing side of a sanitary napkin which is provided with a central bonding pattern that defines lines of weakness.

FIG. 24 shows that another preferred embodiment may feature the insert in a sanitary napkin which has a component, such as the absorbent core which is pre-disposed to deform into a convex upward configuration. Sanitary napkins having components which are pre-disposed to deform into a convex upward configuration are disclosed in U.S. patent application Ser. No. 08/122,114 entitled "Sanitary Napkin Having Core Predisposed to a Convex Upward Configuration" filed Sep. 16, 1993 in the name of Hines, et al. The absorbent core of such products may be pre-disposed to deform into such configurations by providing the sanitary napkin with lines of weakness about which it can bend.

In the version of this embodiment shown in FIG. 24, the sanitary napkin has an absorbent core 42 with at least one transversely-oriented line of weakness 130, such as first line of weakness 130A, formed into its body-facing side (or "first major face") 42A. The line of weakness 130 is concave towards the transverse centerline, T. The sanitary napkin preferably also has a second line of weakness 130B concave towards said first line of weakness 130A (and concave towards the transverse centerline T). Preferably, as shown in FIG. 24, the first and second lines of weakness are connected by longitudinally-oriented, preferably parallel, intermediate lines of weakness 130C. The sanitary napkin may have yet additional lines of weakness such as lines of weakness 130D that are concave away from the longitudinal centerline L.

The first and second lines of weakness 130A and 130B assist the sanitary napkin 20 in deforming into a convex upward configuration at the vaginal orifice and gluteal groove, and in deforming into a concave upward configuration around the mons pubis of the wearer. The additional lines of weakness allow the sanitary napkin to deform into a W-shaped cross-sectional configuration in the central region of the napkin in response to lateral pressure from the thighs of the wearer.

In a preferred embodiment, the lines of weakness 130 are formed by a series of discrete weakened sites (a few of which are shown in FIG. 24). The discrete sites may comprise bonds that join the topsheet and core by heat, compression, or a combination thereof. Suitable technology for forming such discrete bonded sites is disclosed in PCT Publication No. WO 93/11725 published in the name of Cree, et al.

Figure 25:
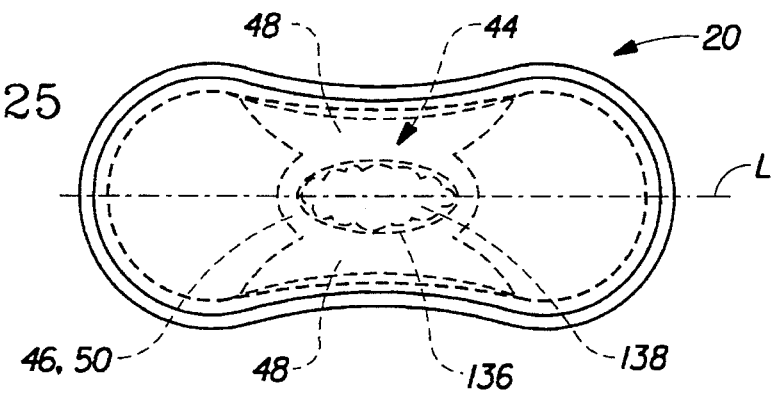
FIG. 25 is a plan view of an alternative sanitary napkin which has an arcuate insert with a window cut-out in the insert.

FIG. 25 shows another alternative embodiment in which the sanitary napkin 20 is provided with a curved absorbent insert 44 having a raised (e.g. arcuate) portion 50 which overlies the absorbent core 42. The sanitary napkin 20 shown in FIG. 25 is provided with a material 138 that fills the space underneath the arcuate portion 50. The space under the arcuate portion 50 is preferably filled with a resilient absorbent material, or at least a material that has liquid distribution capability and which is preferably also resilient. Suitable materials for filling the space under the arcuate portion include many of the materials described as being useful in the absorbent core, including, but not limited to capillary channel fibers, and the like. FIG. 25 also shows that this alternative embodiment may have window 136 cut out of the arcuate portion 50 of the insert 44. The window in the arcuate portion 50 of the insert can be used to place liquid acquisition/distribution material 138 in closer proximity to the wearer's vaginal orifice. The size of such a window 136 and preferred materials for placement with the window are described in U.S. patent application Ser. No. 08/084,048, filed in the name of Doak, et al. on Jun. 28, 1993.

Figure 26:
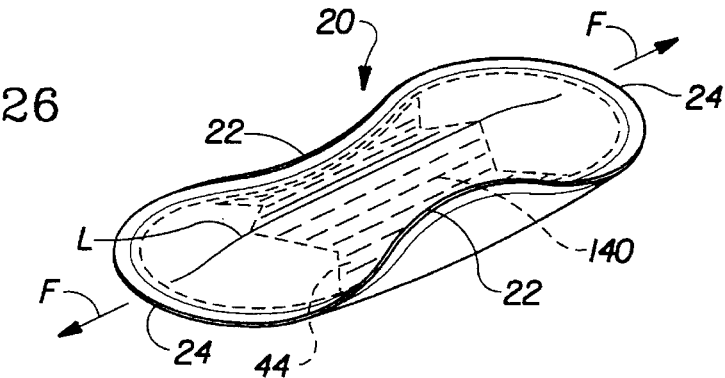
FIG. 26 is a perspective view of an extensible sanitary napkin which has a less extensible insert with a low coefficient of friction on its garment-facing side.

In another alternative embodiment shown in FIG. 26, the topsheet 38, backsheet 40, and absorbent core 42 may comprise extensible components, and the insert 44 is positioned on top of the absorbent core. In this embodiment, the insert 44 of the present invention can be less extensible than the other components of the sanitary napkin and function similarly to the less extensible element described in U.S. Pat. application Ser. No. 07/915,133 (PCT Publication No. WO 93/01785). The lamination of the P-9 material on the bottom of the insert 44, in such an embodiment, provides the insert 44 with a smooth bottom surface (that is, one that has a lower coefficient of friction) so that when the underlying absorbent core 42 is stretched, the insert 44 and the core 42 will be able to more easily slide relative to each other. This is believed to improve the ability of the core 42 to stretch and cause the less extensible insert 44 to pop up.

In embodiments where the insert 44 has a plastic layer for its bottom surface, it is important for the insert 44 to avoid interfering with the absorbent function of the sanitary napkin. There are several ways this can be done. In one version of such an embodiment, the top surface 44A of the insert 44 can comprise sufficient absorbent material that the insert 44 serves as the primary absorbent component of the sanitary napkin in which case it will not be necessary for liquids to be transported through the insert 44. In other versions of such an embodiment, the insert 44 can be made semi-liquid impervious, or liquid impervious and provided with passageways for transporting liquids to an underlying absorbent component. For instance, the insert 44 can be formed of a laminate of TBAL material and a single layer of P-9 material and the P-9 material is not heated until the insert is totally impervious. Alternatively, the insert 44, or the melted P-9 material may be provided with slits shown as 140 in FIG. 26, or have holes punched in it or a window cut out of it so that liquids may travel through the insert 44 to an underlying absorbent component such as the absorbent core 42.

In other alternative embodiments of the present invention, the sanitary napkin 20 may be provided with flaps that extend outwardly from each longitudinal edge 22 of the sanitary napkin 20. The flaps may be in any suitable configuration. Suitable flaps may, for example, be made in accordance with the teachings of U.S. Pat. No. 4,589,876, issued May 20, 1986 to Van Tilburg and U.S. Pat. No. 4,687,478, issued Aug. 18, 1987 to Van Tilburg, U.S. patent application Ser. No. 07/769,891 entitled "Absorbent Article Having Flaps and Zones of Differential Extensibility" filed Oct. 1, 1991 in the name of Lavash, et al. (PCT Publication No. WO 93/06805 published Apr. 15, 1993), U.S. patent application Ser. No. 07/832,246 entitled "Absorbent Article Having Inwardly-Folded Pleated Flaps" filed Feb. 7, 1992 in the name of Niihara, et al., U.S. Ser. No. 07/707,233 entitled "Sanitary Napkin Having Laterally Extensible Means for Attachment to the Undergarment of the Wearer", filed May 21, 1991, in the name of Osborn, et al., and U.S. Pat. No. 5,267,992 issued to Van Tilburg on Dec. 7, 1993.

3. Test Method—Compressive Force and Resiliency Test

The following test method is used to measure the lateral compressibility properties of a sanitary napkin. The sanitary napkin is compressed by a pair of plates designed to simulate forces and constraints experienced during wear. In this test, the center of a sanitary napkin is subjected to 6 cycles of compression along its width, followed by release of the compressive forces. (This test can also be used with other absorbent articles including catamenial products such as pantiliners). The distance of travel of the plates and resulting force are measured.

A. Apparatus and Sample Preparation

Figure 27:
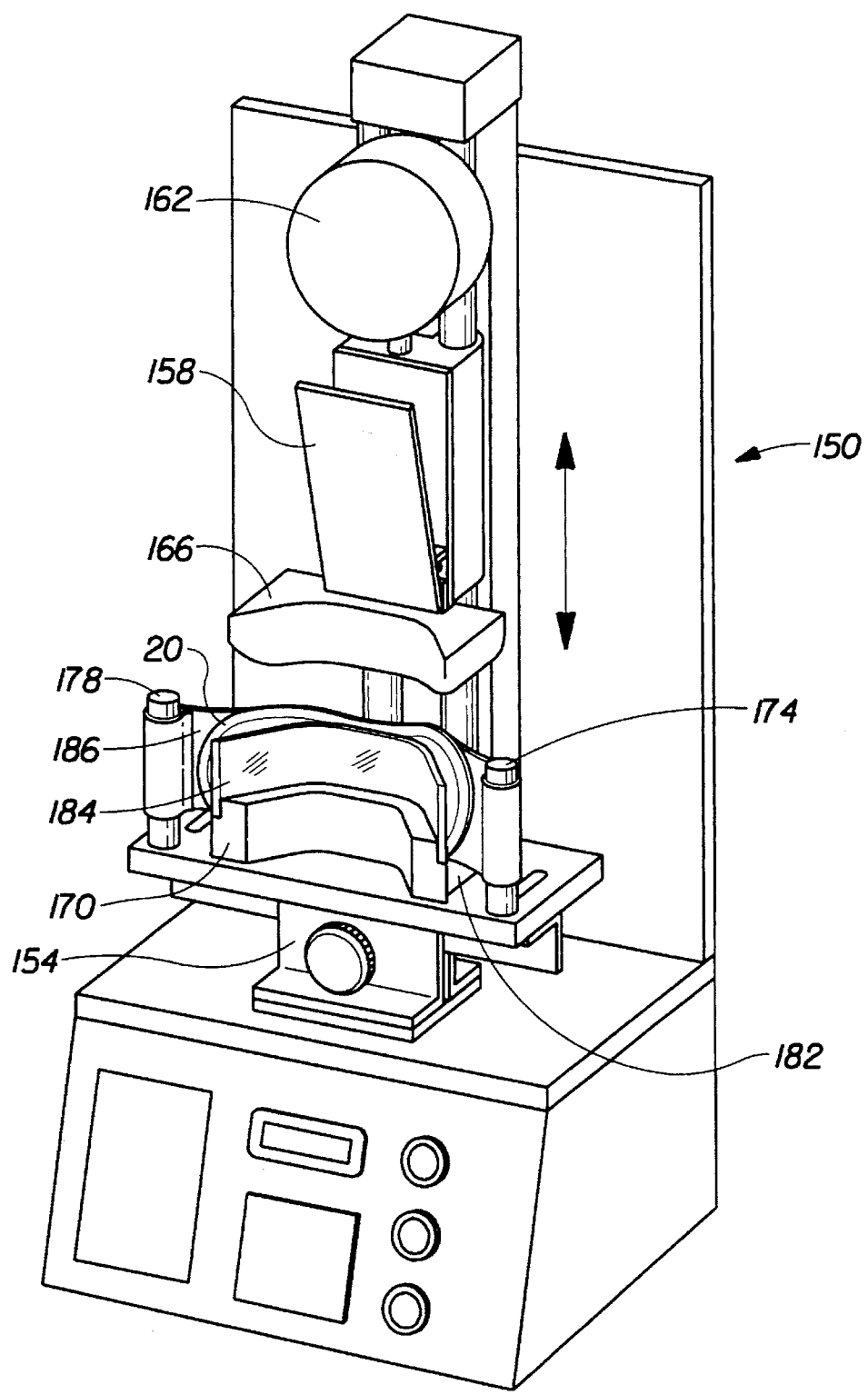
FIG. 27 is a perspective view of an instrument for measuring the compressive force and resiliency of a catamenial pad.

This test requires a constant rate tensile and compression testing apparatus such as an Instron model #1122 or EME 599A tensile (and compression) testing instruments. FIG. 27 shows this test being performed with an EME 599A instrument obtained from EME Inc., P.O. Box 187, Newbury, Ohio, indicated generally as 150.

The testing instrument 150 includes a fixed lower clamp 154 for securing one of the compression plates and an upper reciprocating clamp 158 for securing the other compression plate. Instrument 150 also includes a weight (4000 g) indicated generally as 162 for biasing upper clamp 158 downwardly.

Compressive forces are applied the sanitary napkin 20 by an assembly comprised of a pair of plates 166 and 170. The upper compression plate 166 simulates both the curvature of the opposite thigh of a wearer and the portion of the body contacting the sanitary napkin 20 during use (perineal area). The lower compression plate 170 contains two spaced cylindrical posts 174 and 178, one on each side of the lower body portion 182 of the lower plate 170, as well as a PLEXIGLAS viewing screen 184 mounted on lower body portion 182. These posts 174 and 178 hold the crotch part of a panty 186 for attachment of sanitary napkin 20. (The crotch portion of a suitable panty is cut out from a panty and provided with a sewn tube at either end for attachment to the posts 174 and 178.)

Figure 28:
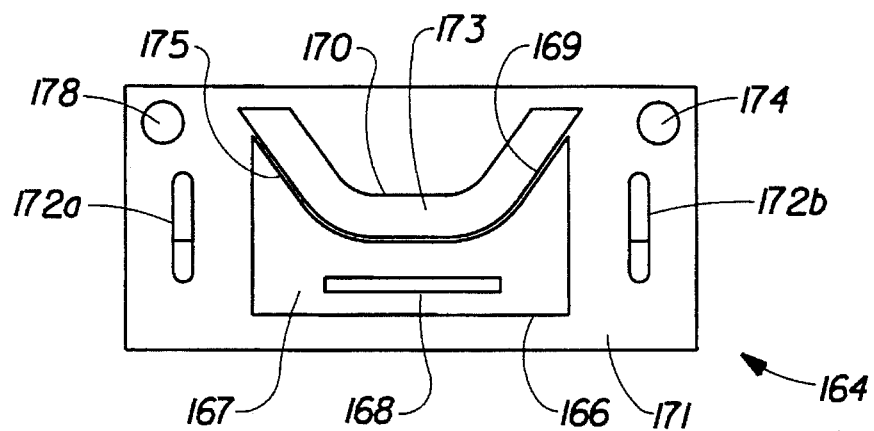
FIG. 28 is a top plan view of the compression plate assembly used in measuring the compressive force and resiliency of the catamenial pad.
Figure 29:
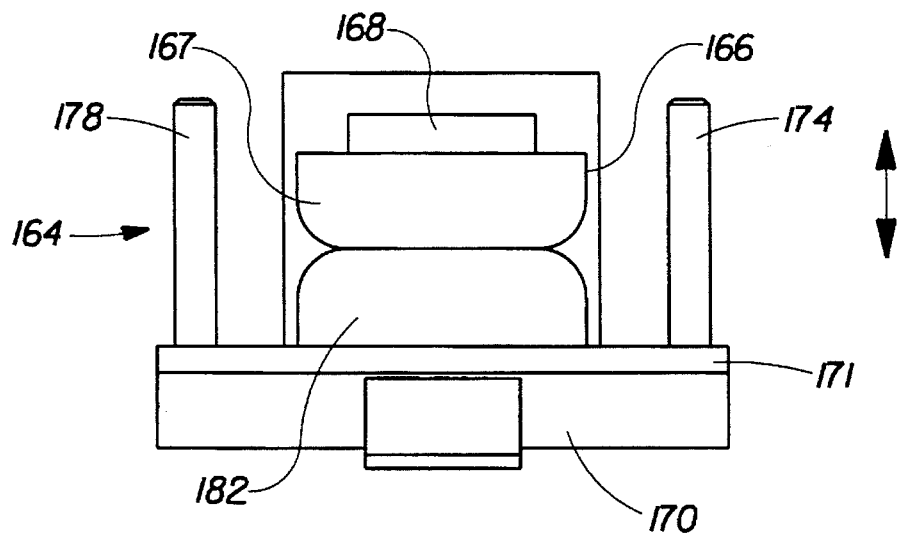
FIG. 29 is a side view of the compression plate assembly shown in FIG. 28.

Plates 166 and 170 are shown in greater detail as assembly 164 in FIGS. 28 and 29. Referring to these Figures, lower plate 170 comprises a base 171 in which are formed a pair of spaced lots 172a and 172b that are used to secure plate 170 to clamp 154 of instrument 150. As particularly shown in FIG. 28, plate 170 has an upper body portion 173 that is provided with a convexly curved face 175.

Figure 30:
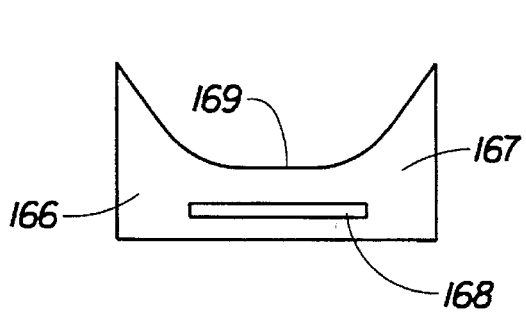
FIG. 30 is a top plan view of the upper compression plate of the compression plate assembly shown in FIGS. 28 and 29.
Figure 31:
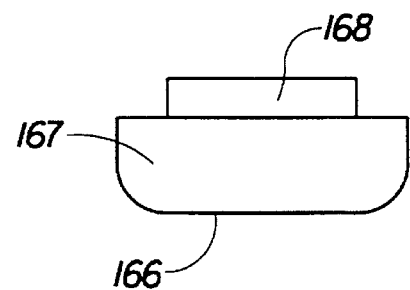
FIG. 31 is a side view of the upper compression plate assembly shown in FIG. 28.

As particularly shown in FIGS. 30 and 31, upper plate 166 has a body portion 167 that is provided with a concave, curved face 169. Attached to body portion 167 is a generally rectangular mounting bracket 168 for securing the upper plate 166 to the reciprocating clamp 158 of instrument 150. As particularly shown in FIG. 28, curved convex face 175 of lower plate 170 forms a matable configuration with curved concave face 169 of upper plate 166. This matable configuration allows upper plate 166 to move past lower plate 170 in close proximity thereof, but without contact.

The plates 166 and 170 (and their constituent parts) can be made from any suitable material that can be formed into the required shape (e.g., aluminum, LEXAN, PLEXIGLAS). The weight of the plates 166 and 170 together must be significantly lower than the limit of the instrument load cell to allow sufficient range for the force measurement. The plates 166 and 170 should also be centered with the curvatures of the upper and lower pieces lined up opposite one another. When the plates come together during compression, there should be no physical contact between them.

During the test, the crosshead speed is 22 inches/minute (56 cm/minute). The gap between plates 166 and 170 starts at a distance of 4 inches (10 cm), and then narrows to a 1 inch (2.54 cm) gap distance when sanitary napkin 20 is fully compressed. This equates to an initial cross head setting of 20 cm and a final crosshead setting of 12.5 cm when the dimensions of the apparatus are taken into account.

Samples of sanitary napkin 20 are equilibrated for a minimum of two hours at 73 ±2° F., and 50±2% relative humidity. Samples should be fully finished sanitary napkins, including placement of adhesive and release paper on the bottom of the sanitary napkin. Undue bending of the sample as it is being prepared should be avoided.

B. Test Procedure

A minimum of six samples of each sanitary napkin 20 are required for the test. The release paper is removed from the sanitary napkin 20 and then the sanitary napkin is centered on the panty crotch portion with respect to the seams. The sanitary napkin 20 is then pressed down lightly to ensure it is secured. The sewn tubes on the ends of the panty crotch portion are then slid onto the poles of lower compression plate 170. Sanitary napkin 20 should be in the configuration of an arc with it ends pointing toward the front of instrument 150, and should be loosely confined between the panty crotch and the lower front portion of plate 170. The sanitary napkin 20 is oriented such that it is standing up on one edge. The plates 166 and 170 should now be 4 inches apart.

The plate 166 is then moved towards plate 170 by the downward motion of reciprocating upper clamp 158 until sanitary napkin 20 has been compressed to 1 inch (full compression). Compression is then maintained for 30 seconds. The distance at which the upper compression plate 166 makes contact with the edge of sanitary napkin 20 is determined when a force of 10 g is reached. This is the initial width of the sanitary napkin. The force at the end of the 30 seconds after full compression is reached, and immediately before the compression is released, is recorded as the compression force.

After 30 seconds of full compression, the compressive forces are released by moving plate 166 to its initial position (4 inches apart). Sanitary napkin 20 is left uncompressed for 60 seconds. At the end of 60 seconds, a second compression cycle is started. The same procedure described before is carried out. This procedure is repeated until sanitary napkin 20 has been subjected to 6 compression/release cycles.

Three dry samples of sanitary napkin 20 are tested by this procedure. Three additional samples of sanitary napkin 20 are then tested in the wet state by pouring 7.5 ml of 0.9% saline solution into the center of the samples (allowing the sample to distribute the fluid itself), followed by 10 minutes before testing begins. The wet samples are subjected to the same procedure as the dry samples.

C. Calculations

After three dry samples and three wet samples are run, the following values are determined:

(1) The average compression force from cycle 6 on the three dry sanitary napkins;

(2) The average initial sanitary napkin width from cycle 6 on the three wet sanitary napkins;

(3) The average percent width on the three wet sanitary napkins is calculated using the following equation % sanitary napkin width=100×(initial sanitary napkin width cycle 6÷initial sanitary napkin width cycle 1)

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article for wearing in the crotch region of an undergarment, said absorbent article having a longitudinal centerline oriented in a longitudinal direction, a transverse centerline, a first end region, a second end region, and a central region disposed between said end regions, said absorbent article comprising:

a liquid pervious topsheet;

a liquid impervious backsheet joined with said topsheet; and an absorbent core disposed between said topsheet and said backsheet wherein said absorbent article comprises a resilient portion that is resilient to transversely inwardly-oriented forces, said resilient portion being located in the central region of the absorbent article, said resilient portion comprising a central body, a pair of lateral side portions, a pair of longitudinal side edges and a pair of end edges, wherein at least one of said end edges has points of maximum displacement in the longitudinal direction and said end edge has gaps that are spaced longitudinally inward from said points of maximum displacement of said end edge, wherein said resilient portion has a substantially continuous transverse cross section longitudinally inboard of said gaps and said at least one of said end edges has an extension formed by said central body and at least one extension formed by one of said lateral side portions, and at least one gap is formed between said extension formed by said central body and said extension formed by said at least one of said lateral side portions.

2. The absorbent article of claim 1 wherein said gaps comprise slits.

3. The absorbent article of claim 1 wherein said gaps comprise notches.

4. The absorbent article of claim 1 wherein said at least one of said end edges of said resilient portion has a "W"-shape when said resilient portion is viewed from a plan view.

5. The absorbent article of claim 4 wherein said W-shape end has a hump portion formed by said central body and said hump is rounded and convex away from said transverse centerline.

6. The absorbent article of claim 4 wherein both of said end edges of said resilient portion are W-shaped.

7. The absorbent article of claim 1 wherein said longitudinal side edges of said resilient portion are concave inward.

8. The absorbent article of claim 1 wherein said resilient portion is generally planar before it is subjected to forces when said absorbent article is in use.

9. The absorbent article of claim 8 wherein said central body of said resilient portion assumes a convex upward configuration and said lateral side portions bend upward when said absorbent article is subjected to lateral compressive forces.

10. The absorbent article of claim 9 wherein said resilient portion assumes a rounded "W"-shaped cross-sectional configuration when said absorbent article is subjected to lateral compressive forces.

11. The absorbent article of claim 1 wherein said resilient portion comprises at least one component of said absorbent article that is provided with first regions and second regions, wherein said first regions are stiffer than said second regions and said second regions are flexible enough so that said component can be bent about said second regions.

12. The absorbent article of claim 11 wherein said first regions of said resilient component have a material attached thereto so that said first regions are stiffer than said second regions.

13. The absorbent article of claim 11 wherein said first regions of said resilient component are at least partially melted so that said first regions are stiffer than said second regions.

14. The absorbent article of claim 1 wherein said resilient portion is pre-formed into a three-dimensional shape.

15. The absorbent article of claim 1 wherein said absorbent article is provided with at least one deformation zone.

16. The absorbent article of claim 15 wherein said absorbent article comprises at least one deformation line.

17. The absorbent article of claim 16 wherein said deformation line is continuous.

18. The absorbent article of claim 16 wherein said deformation line is intermittent.

19. The absorbent article of claim 16 wherein said resilient portion comprises a resilient component that is a separate insert positioned between said topsheet and backsheet.

20. The absorbent article of claim 19 wherein said resilient component has a longitudinal centerline, a body surface, and a garment surface, and said central body of said resilient component has a pair of ends, and said at least one deformation line is formed in said garment surface of said component and extends between said ends of said resilient component.

21. The absorbent article of claim 20 wherein said resilient component has at least one deformation line formed in its body surface, and said deformation line is oriented in the longitudinal direction and runs between said central body of said resilient component and one of said lateral side portions of said resilient component.

22. The absorbent article of claim 21 wherein there are two deformation lines, one between said central body of said resilient component and each lateral side portion and said deformation lines are concave toward said longitudinal centerline.

23. The absorbent article of claim 1 wherein said central body of said resilient portion overlies at least one underlying component of said absorbent article and said at least part of said central body of said resilient portion is unattached to said central body so that said unattached portion of said central body can decouple from said underlying component.

24. The absorbent article of claim 23 having a garment-facing side and further comprising a fastener on said garment-facing side for fastening the absorbent article to the crotch region of said undergarment wherein said fastener is provided in two modified "V"-shaped patterns each having a pair of legs, one of which is located in each end region of said absorbent article and being oriented so that said modified "V"-shaped patterns are centered relative to said longitudinal centerline and each modified "V"-shaped pattern has a base which is closer to said transverse centerline than other portions of said "V"-shaped pattern and an open space between each of the legs in said pair of legs.

25. An absorbent article according to claim 1 wherein said topsheet, said backsheet and said absorbent core are extensible and said absorbent core has a body-facing side and a garment-facing side; and said resilient portion comprises a resilient insert positioned between said topsheet and said absorbent core in at least said central region of said absorbent article, said resilient insert being less extensible than said absorbent core and having a body-facing side and a garment-facing side wherein said garment-facing side is provided with a lower coefficient of friction than said absorbent core so that said insert may slip against the body-facing side of said absorbent core when said absorbent article extends.

26. An absorbent article for wearing in a crotch region of an undergarment, said absorbent article having a longitudinal centerline oriented in a longitudinal direction, a transverse centerline, a first end region, a second end region, and a central region disposed between said end regions, said absorbent article comprising:

a liquid pervious topsheet;

a liquid impervious backsheet joined with said topsheet; and an absorbent core disposed between said topsheet and said backsheet; and a resilient portion that is resilient to transversely inwardly-oriented forces, said resilient portion being located in the central region of the absorbent article, said resilient portion comprising at least one component of said absorbent article and further comprising a central body, a pair of lateral side portions, a pair of longitudinal side edges and a pair of end edges, wherein at least one of said end edges has points of maximum displacement in the longitudinal direction and said end edge has gaps between said central body and said lateral side portions that are spaced longitudinally inward from said points of maximum displacement of said end edge, wherein said resilient portion has a substantially continuous transverse cross section longitudinally inboard of said gaps and said at least one of said end edges has an extension formed by said central body and at least one extension formed by one of said lateral side portions, and at least one gap is formed between said extension formed by said central body and said extension formed by said at least one of said lateral side portions.

27. The absorbent article of claim 26 wherein said resilient component comprises three arcuate portions when viewed in a cross-section taken along a transverse line, said arcuate portions having transition areas therebetween and comprising:

(a) a convex-upward central arcuate portion comprised of at least a portion of the central body of said resilient component, wherein said central arcuate portion defines a hump;

(b) a first concave upward lateral arcuate portion comprising a first lateral side portion and at least a portion of the transition between said central body and said first lateral side portion;

(c) a second concave upward lateral arcuate portion comprising the other lateral side portion and at least a portion of the transition between said central body and said second lateral side portion.

28. The absorbent article of claim 27 wherein said arcuate portions define a rounded "W"-shape cross-section which comprises one continuous curve from one longitudinal side edge of said resilient component to the other longitudinal side edge.

29. The absorbent article of claim 28 wherein said central body has a front end and a back end and said central body has a convex upward arcuate configuration from said front end to said back end.

30. The absorbent article of claim 27 further comprising at least one deformation zone.

31. The absorbent article of claim 27 further comprising material positioned beneath the hump defined by said convex upward central arcuate portion to fill the space underneath said hump.

32. The absorbent article of claim 31 wherein said material positioned beneath said hump is resilient.

33. The absorbent article of claim 32 wherein said material positioned beneath said hump is absorbent.

34. The absorbent article of claim 31 wherein said central arcuate portion has a window cut out therein.

35. The absorbent article of claim 26 wherein said resilient component comprises an insert that is positioned between said topsheet and said absorbent core.

36. The absorbent article of claim 26 wherein said resilient component comprises at least a portion of said absorbent core.

37. The absorbent article of claim 26 wherein said resilient component is positioned between said absorbent core and said backsheet.

38. The absorbent article of claims 1 or 26 wherein said resilient portion at least partially comprises an absorbent material.

39. The absorbent article of claim 38 wherein said absorbent material comprising said resilient portion comprises a thermally bonded airlaid web.

40. The absorbent article of claim 26 wherein said resilient component has a caliper of less than or equal to about 1.25 mm.

41. The absorbent article of claim 40 comprising a sanitary napkin having a caliper of less than or equal to about 3 mm.

\* \* \* \* \*